(12) United States Patent
Li et al.

(10) Patent No.: US 9,402,819 B2
(45) Date of Patent: Aug. 2, 2016

(54) ANTI-HIV COMPOUND AND PREPARATION METHOD AND USE THEREOF

(71) Applicant: Sichuan University, Chengdu (CN)

(72) Inventors: Rui Li, Chengdu (CN); Yuquan Wei, Chengdu (CN)

(73) Assignee: Sichuan University, Chengdu (CN)

( * ) Notice: Subject to any disclaimer, the term of this patent is extended or adjusted under 35 U.S.C. 154(b) by 0 days.

(21) Appl. No.: 14/647,159

(22) PCT Filed: Dec. 13, 2013

(86) PCT No.: PCT/CN2013/089341
§ 371 (c)(1),
(2) Date: May 26, 2015

(87) PCT Pub. No.: WO2014/079398
PCT Pub. Date: May 30, 2014

(65) Prior Publication Data
US 2015/0313853 A1 Nov. 5, 2015

(30) Foreign Application Priority Data

Nov. 26, 2012 (CN) .......................... 2012 1 0484783

(51) Int. Cl.
| | | |
|---|---|---|
| *A61K 31/10* | (2006.01) | |
| *A61K 31/167* | (2006.01) | |
| *A61K 31/18* | (2006.01) | |
| *A61K 31/495* | (2006.01) | |
| *A61K 31/5375* | (2006.01) | |
| *A61K 31/683* | (2006.01) | |
| *A61K 31/255* | (2006.01) | |
| *C07C 323/62* | (2006.01) | |
| *C07C 317/48* | (2006.01) | |
| *C07C 317/50* | (2006.01) | |
| *C07C 323/63* | (2006.01) | |
| *C07C 237/44* | (2006.01) | |
| *C07F 9/40* | (2006.01) | |

(52) U.S. Cl.
CPC ............... *A61K 31/167* (2013.01); *A61K 31/18* (2013.01); *A61K 31/255* (2013.01); *A61K 31/495* (2013.01); *A61K 31/5375* (2013.01); *A61K 31/683* (2013.01); *C07C 237/44* (2013.01); *C07C 317/48* (2013.01); *C07C 317/50* (2013.01); *C07C 323/62* (2013.01); *C07C 323/63* (2013.01); *C07F 9/4056* (2013.01)

(58) Field of Classification Search
USPC .......................................... 514/708, 741, 613
See application file for complete search history.

(56) References Cited

U.S. PATENT DOCUMENTS

2007/0099919 A1 * 5/2007 Rana .................... A61K 31/165
514/237.5

FOREIGN PATENT DOCUMENTS

| CN | 102603585 A | 7/2012 |
|---|---|---|
| CN | 103183625 A | 7/2013 |
| WO | 0216356 A2 | 2/2002 |
| WO | 2007044565 A2 | 4/2007 |
| WO | 2010123591 A2 | 10/2010 |
| WO | 2012097550 A1 | 7/2012 |

OTHER PUBLICATIONS

Nielsen et al., "2-(4-Methoxyphenoxy)-5-nitro-N-(4-sulfamoylphenyl)benzamide activates Kir6.2/SUR1 Katp channels", Bioorganic & Medical Chemistry Letters, vol. 14, pp. 5727-5730 (2004).
International Search Report for PCT/CN2013/089341 dated Mar. 6, 2014.

* cited by examiner

*Primary Examiner* — Pancham Bakshi
(74) *Attorney, Agent, or Firm* — Caesar Rivise, PC

(57) ABSTRACT

The present invention relates to the technical field of chemically synthesized drugs, in particular to an anti-HIV drug or prodrug and preparation method and uses thereof. The compound or prodrug compound of the present invention has a structural formula as represented by formula I. The compounds have anti-HIV-1 and anti-HIV-2 virus activity, and have a C8166 therapeutic index as high as 2081.59 and an H9 therapeutic index as high as 303.03. Furthermore, the compounds have high solubility up to 1290-2845.5 μg/ml in an aqueous solution, and can be formulated into an oral formulation.

10 Claims, 3 Drawing Sheets

Intravenous administration 100mg/kg

Oral administration 50mg/kg

ANTI-HIV COMPOUND AND PREPARATION METHOD AND USE THEREOF

FIELD OF THE INVENTION

The present invention relates to the technical field of chemically synthesized drugs, in particular to an anti-HIV drug or prodrug and preparation method and uses thereof.

BACKGROUND OF THE INVENTION

Acquired immune deficiency syndrome (AIDS), which disseminates quickly in the world, has become significant public health event and social hot spot.

AIDS was identified as a disease in 1981 by Centers for Disease Control and Prevention of USA. China experienced its first case of AIDS in 1985. In the past two decades, more and more cases were reported. Nowadays, it has already been spread in many areas of the world. Since China is a country of vast territory and large population, together with the recently frequent international contacts, the number of HIV infections increased year by year. AIDS is a spectrum of conditions caused by the human immunodeficiency virus (HIV), with poor prognosis and high mortality rate. According to the related report of UNAIDS, the population of HIV infections around the world is more than 39 million. Nowadays, India takes over South Africa as the largest population of HIV-infected individuals in the world.

Thus, finding a way to stop the spread of AIDS has become the focus of the world. Most of the Anti-AIDS drugs in clinic are HIV-1 reverse transcriptase inhibitors and HIV-1 protease inhibitors at present time. In humans, the apolipoprotein B mRNA-editing enzyme catalytic polypeptidelike 3G (APOBEC3G, A3G) is a major host-cell factor which can severely weaken the infectivity of HIV-1. It was proved that HIV-1 viral infectivity factor (Vif) can protect the virus from A3G-mediated viral cDNA hypermutation. Therefore, to protect A3 G from degradation, it is very crucial to design inhibitors targeting Vif. In addition, development of multi-target inhibitor of Vif accompanied by other enzymes may improve the therapeutic effect and reduce the virus resistance.

The inventor of this invention endeavored to find the new HIV inhibitors. The inventor has synthesized a series of N-phenyl-2-thiophenylbenzamide derivatives and N-phenyl-2-thiol benzamide derivatives as following:

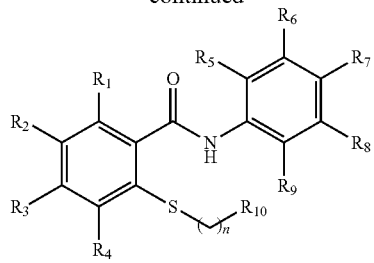

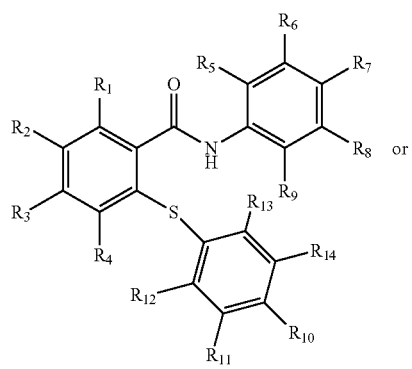

However, those compounds show general activity, high cytotoxicity, poor solubility and low bioavailability which restrict its application.

In the follow-up project, the inventor found that $R_1$ or $R_2$ substituted by —$NH_2$ or —$NH_2$—R can obviously improve the anti-HIV activity, solubility, druggability and reduce drug toxicity.

SUMMARY OF THE INVENTION

One embodiment of the present invention is directed to a new HIV inhibitor of formula (I) or its pharmaceutically acceptable salt.

In one embodiment, the HIV inhibitors of the present invention have the following structural formula (I):

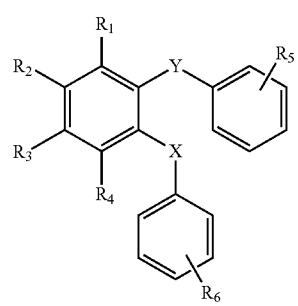

Formula (I)

wherein:

X is selected from the group consisting of: S, SO, $SO_2$, $NR_7$, $CH_2$ or O;

Y is selected from the group consisting of: $CONR_7$, $NR_7CO$, $SO_2NR_7$ or $NR_7SO_2$;

$R_1$, $R_2$, $R_3$ and $R_4$ are independently selected from the group consisting of: H, $NO_2$,

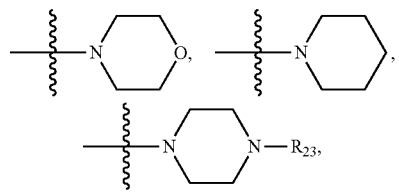

$NR_{15}R_{16}$ or $CF_3$, and $R_1$, $R_2$, $R_3$ and $R_4$ cannot be H in same time;

$R_5$ is selected from the group consisting of: H, $C_{1-8}$ alkoxy, $C_{1-8}$ alkanoyl, $C_{1-8}$ alkylamino, $C_{1-8}$ alkyl, OH, $NO_2$, halogen, COOH,

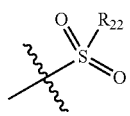

or NH$_2$;

R$_6$ is selected from the group consisting of: H, NO$_2$, C$_{1-8}$ alkoxy, C$_{1-8}$ alkanoyl, C$_{1-8}$ alkylamino, C$_{1-8}$ alkyl, OH, COOH, halogen or NH2;

R$_7$ is selected from the group consisting of: H or C$_{1-8}$ alkyl;

R$_{15}$ and R$_{16}$ are independently selected from the group consisting of: H, CH$_3$, C$_{1-8}$ alkanoyl,

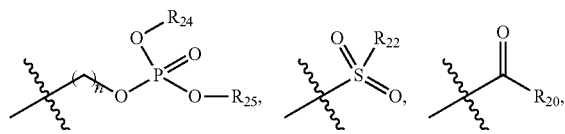

C$_{1-8}$ alkyl, -A-NH$_2$, -A-OH, -A-halogen or

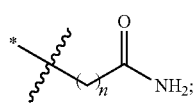

A is C1-8 alkyl; n=0, 1 or 2;

R$_{20}$ is selected from the group consisting of: aryl, substituted aryl, heteroaryl, substituted heteroaryl, which can hydrolyze inside of body.

R$_{22}$ is selected from the group consisting of: H, C$_{1-8}$ alkyl, aryl or substituted aryl;

R$_{23}$, R$_{24}$ and R$_{25}$ are independently selected from the group consisting of: H, C$_{1-8}$ alkyl, C$_{1-8}$ alkanoyl or substituted C$_{1-8}$ alkanoyl;

The term "substituted" as used herein refers to NO$_2$, NH$_2$, OH, CF$_3$, halogen, carboxyl, C1-8 alkoxy, C1-8 alkanoyl, C1-8 alkylamino, C1-8 alkyl;

The term "alkanoyl" as used herein refers to a straight, branched or cyclic alkanoyl group attached to acyl (alkyl-CO—). "C1-8 alkanoyl" refers to an alkanoyl group which has 1-8 carbon atom(s). Exemplary alkanoyl groups include, but are not limited to acetyl, propanoyl, isopropanoyl, butanoyl, etc.

The term "alkoxy" as used herein refers to a straight or branched alkyl group attached to oxygen (alkyl-O—). "C1-8 alkoxy" refers to an alkoxy group which has 1-8 carbon atom(s). Exemplary alkoxy groups include, but are not limited to methoxy, ethoxy, isopropoxy, etc.

The term "alkylamino" as used herein refers to a straight or branched alkyl group attached to amidogen (alkyl-NH$_2$—). "C1-8 alkylamino" refers to an alkylamino group which has 1-8 carbon atom(s).Exemplary alkylamino groups include, but are not limited to methylamino, ethylamino, 1-propanamine,isopropylamine, n-butylamine, etc.

The term "alkyl" as used herein refers to a straight, branched or cyclic. "C$_{1-8}$ alkyl" refers to an alkyl group which has 1-8 carbon atom(s). Exemplary "alkyl" groups include, but are not limited to methyl, ethyl, 1-propyl, 2-propyl, 2-methyl-1-propyl, 2-methyl-2-propyl, 1-butyl, 2-butyl, 1-pentyl, 2-pentyl, 3-pentyl, 2-methyl-1-butyl, 3-methyl-1-butyl, 3-methyl-2-butyl, 2,2-dimethyl-1-propyl, 1-hexyl, 1-heptyl, n-heptyl, etc.

In another embodiment of the invention, HIV inhibitor compounds have the following structural formula (II):

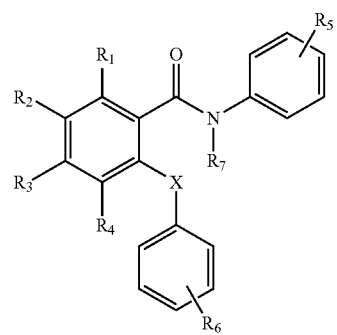

Formula (II)

According to knowledge of bioisostere and molecular similarity, Y=CONR$_7$, Y=NR$_7$CO, Y=SO$_2$NR$_7$ and Y=NR$_7$SO$_2$ show the similar structure and activity.

In further optimize embodiment of the invention, HIV inhibitor compounds have the following structural formula (III):

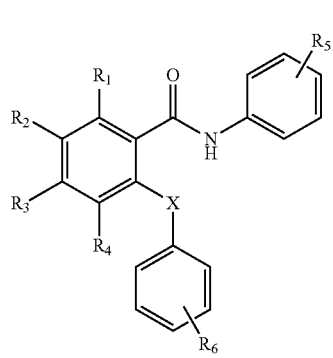

Formula (III)

In another embodiment of the invention, HIV inhibitor compounds have the following structural formula (III-1), characterized in that R$_1$=NR$_{15}$R$_{16}$, R$_2$—R$_4$=H;

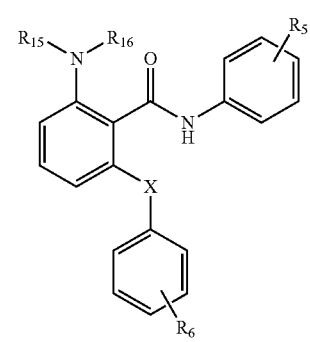

Formula (III-1)

Wherein:

R$_5$ is selected from the group consisting of: C$_{1-8}$ alkoxy, halogen, carboxyl,

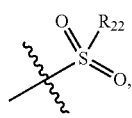

$C_{1-8}$ alkyl or $NH_2$;

$R_6$ is selected from the group consisting of: $NO_2$, $NH_2$, $C_{1-8}$ alkyl or carboxyl;

X is selected from the group consisting of: S, SO, $SO_2$ or O, and particularly X=S or $SO_2$.

In another embodiment of the invention, HIV inhibitor compounds have the following structural formula (III-11), characterized in that $R_{15}$=H, $R_{16}$=H,

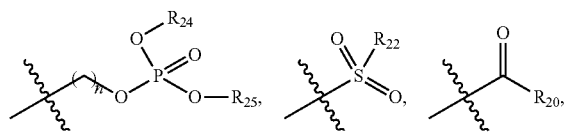

$C_{1-8}$ alkyl, -A-$NH_2$, -A-OH, -A-halogen or

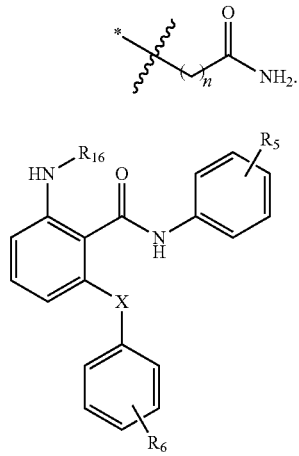

Formula (III-11)

In another embodiment of the invention, HIV inhibitor compounds have the following structural formula (III-11), characterized in that

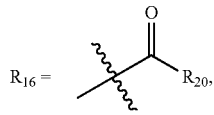

$R_{20}$=aryl, substituted aryl, heteroaryl, substituted heteroaryl, which can has hydrolyzed inside of body.

Another embodiment of the present invention relates to the compound of formula (III-11), characterized in that $R_{20}$ is single amino acid or peptide;

the amino acid residue directly connected to the carbonyl group is lack of α-C carboxyl like

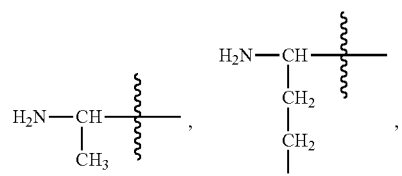

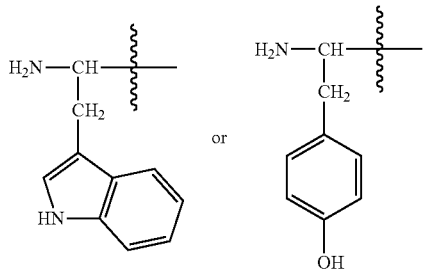

etc.

wherein the "amino acid" can be Ala, Arg, Asn, Asp, Cys, Glu, Gln, Gly, His, Ile, Leu, Lys, Met, Phe, Pro, Ser, Thr, Trp, Tyr, Val; and particularly Phe, Gly, Lys. (compound 66, 67, 68, 83)

The ideal way of administration for AIDS drugs is oral. Generally, oral bioavailability has close relationship with the solubility. In this invention, although the derivative 46 with $R_1$=$NH_2$ shows the strongest antiviral activity, it bears the general solubility. In order to improve the oral bioavailability, the inventor used those amino acids to react with the amine group and acquired the corresponding prodrugs. Those prodrugs can be hydrolyzed to form the active compounds in the body. For example, compound 67 can be hydrolyzed to generate the active compound 46.

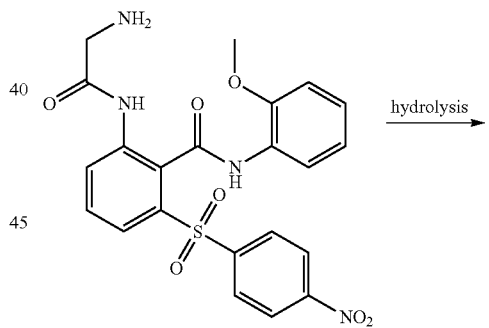

67

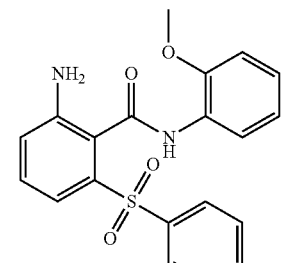

46

Another embodiment of the present invention relates to the compound of formula (III-11), characterized in that $R_{20}$ is aryl, substituted aryl, heteroaryl or substituted heteroaryl and particularly $R_{20}$ is aryl or substituted aryl; X=S, SO, $SO_2$ or O, and particularly X=S or $SO_2$.

The term "substituted" as used herein refers to $NO_2$, $NH_2$, OH, $CF_3$, halogen, carboxyl, $C_{1-8}$ alkoxy, $C_{1-8}$ alkanoyl, $C_{1-8}$ alkylamino, $C_{1-8}$ alkyl;

The term "alkanoyl" as used herein refers to a straight, branched or cyclic alkanoyl group attached to acyl (alkyl-CO—).

The term "alkoxy" as used herein refers to a straight or branched alkyl group attached to oxygen (alkyl-O—).

The term "alkylamino" as used herein refers to a straight or branched alkyl group attached to amidogen (alkyl-$NH_2$—).

The term "alkyl" as used herein refers to a straight, branched or cyclic.

Another embodiment of the present invention relates to the compound of formula (III-11), characterized in that $R_{16}$=H, structural format is as follows:

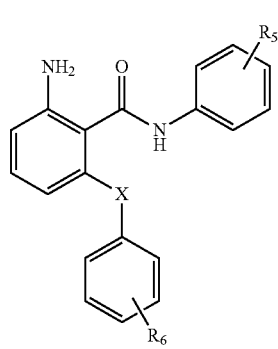

Formula (III-11-1)

Another embodiment of the present invention relates to the compound of formula (III-11-1), characterized in that $R_6$ is 4-substituted $NO_2$ or COOH, structural format is as follows:

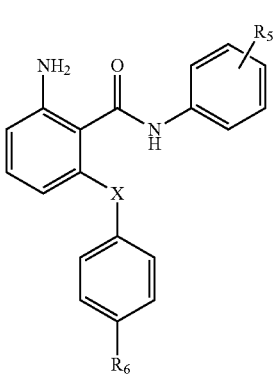

Formula (III-11-11)

Another embodiment of the present invention relates to the compound of formula (III-11-11), $R_5$ is 2-substituted, structural format is as follows:

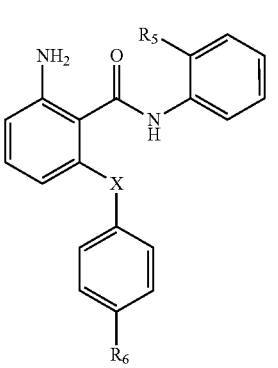

Formula (III-11-111)

Wherein:

$R_5$ is H, $C_{1-8}$ alkoxy, halogen, carboxyl,

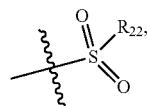

$C_{1-8}$ alkyl or $NH_2$;

The term "alkoxy" as used herein refers to a straight or branched alkyl group attached to oxygen (alkyl-O—).

The term "alkyl" as used herein refers to a straight, branched or cyclic;

X is S, SO, $SO_2$ or O, and particularly X=S or $SO_2$.

Another embodiment of the present invention relates to the compound of formula (III-11-111), characterized in that $R_6$=$NO_2$, structural format is as follows:

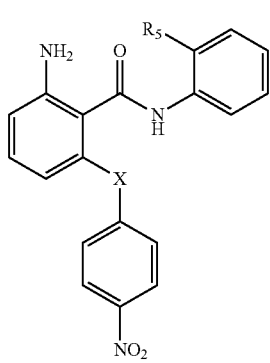

Formula (III-11-1111)

Wherein:

when $R_5$ is $C_{1-8}$ alkoxy, the term "alkoxy" as used herein refers to a straight or branched alkyl group attached to oxygen (alkyl-O—), and particularly $R_5$=methoxyl; X=S, $SO_2$ or O; (compound 25, 46, 48)

when $R_5$ is halogen, the term "halogen" as used herein refers to F, Cl, Br or I, and particularly $R_5$=I; X=S or $SO_2$; (compound 71, 72)

when $R_5$ is carboxyl, X=S or $SO_2$;

when $R_5$ is

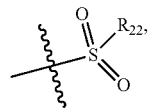

$R_{22}$ is H or $C_{1-8}$ alkyl particularly $R_{22}$=methyl; X=S or $SO_2$; (compound 73)

when $R_5$ is $C_{1-8}$ alkyl particularly $R_5$=methyl; X=S or $SO_2$;

when $R_5$=$NH_2$; X=S or $SO_2$.

Another embodiment of the present invention relates to the compound of formula (III-11-11), characterized in that $R_6$=COOH, structural format is as follows:

Formula (III-11-112)

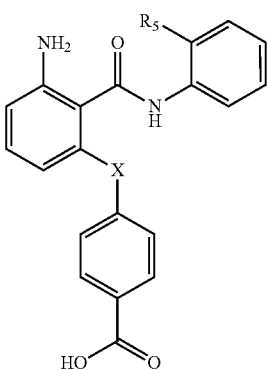

Wherein $R_5$ is $C_{1-8}$ alkoxy particularly $R_5$=methoxyl; X=S or $SO_2$. (compound 76, 77)

Another embodiment of the present invention relates to the compound of formula (III-11-11), characterized in that $R_6$=$NO_2$, $R_5$ is 2-substituted or 4-substituted, structural format is as follows:

Formula (III-11-113)

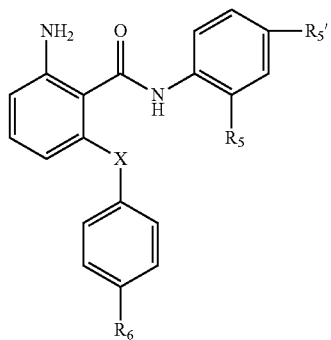

Wherein:
$R_5$ is $C_{1-8}$ alkoxy particularly $R_5$=methoxyl;
$R_5'$ is $C_{1-8}$ alkoxy or $NH_2$ particularly $R_5$=methoxyl;
X=S or $SO_2$. (compound 50, 51)

Another embodiment of the present invention relates to the compound of formula (III-11-11), characterized in that $R_5$ is 3-substituted, structural format is as follows:

Formula (III-11-114)

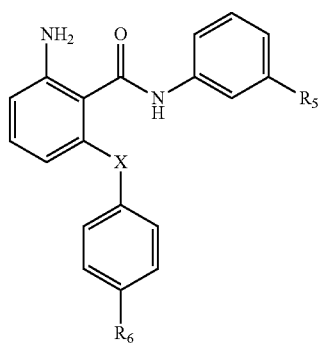

Wherein:
$R_6$ is $NO_2$;
$R_5$ is $C_{1-8}$ alkoxy particularly $R_5$=methoxyl; X=S, $SO_2$ or O;

when $R_5$ is halogen, the term "halogen" as used herein refers to F, Cl, Br or I, and particularly $R_5$=I; X=S or $SO_2$;
when $R_5$ is carboxyl, X=S or $SO_2$;
when $R_5$ is

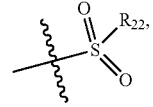

$R_{22}$ is H or $C_{1-8}$ alkyl particularly $R_{22}$=methyl; X=S or $SO_2$;
when $R_5$ is $C_{1-8}$ alkyl particularly $R_5$=methyl; X=S or $SO_2$;
when $R_5$=$NH_2$; X=S or $SO_2$. (compound 49)

Another embodiment of the present invention relates to the compound of formula (III-11-1), characterized in that $R_6$ is 3-substituted and 5-substituted, structural format is as follows:

Formula (III-11-12)

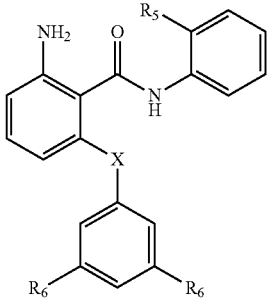

Wherein:
$R_6$ and $R_6'$ are independently selected from the group consisting of: $C_{1-8}$ alkyl and particularly $R_6$ and $R_6'$=methyl;
$R_5$ is $C_{1-8}$ alkoxy particularly $R_5$=methoxyl; X=S or $SO_2$; (compound 75)

Another embodiment of the present invention relates to the compound of formula (III-11); characterized in that $R_{16}$ is

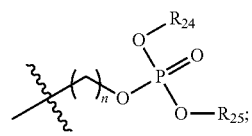

$R_{24}$ and $R_{25}$ are independently selected from the group consisting of: H or $C_{1-8}$ alkyl, and particularly $R_{24}$ and $R_{25}$ are independently as

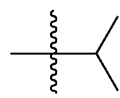 [SMILES: *C(C)C]

X=S or $SO_2$. (Compound 65)

Another embodiment of the present invention relates to the compound of formula (III-11); characterized in that $R_{16}$ is

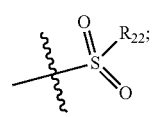

$R_{22}$ is H, $C_{1-8}$ alkyl, aryl or substituted aryl; The term "substituted" as used herein refers to $NO_2$, $NH_2$, OH, $CF_3$, halogen, carboxyl, $C_{1-8}$ alkyl; particularly $R_{22}$=methyl; X is S, SO, $SO_2$ or O, and particularly X=S or $SO_2$. (Compound 56, 57, 60, 61)

Another embodiment of the present invention relates to the compound of formula (III-11);characterized in that $R_{16}$ is $C_{1-8}$ alkyl, particularly $R_{16}$=methyl; X is S, SO, $SO_2$ or O, and particularly X=S or $SO_2$. (Compound 59)

Another embodiment of the present invention relates to the compound of formula (III-11);characterized in that $R_{16}$= $C_{1-8}$ alkyl-$NH_2$, particularly $R_{16}$=—$(CH_2)_2$—$NH_2$; X is S, SO, $SO_2$ or O, and particularly X=S or $SO_2$. (compound 78, 79)

Another embodiment of the present invention relates to the compound of formula (III-11);characterized in that $R_{16}$= $C_{1-8}$ alkyl-OH, particularly $R_{16}$=—$(CH_2)_2$—OH; X is S, SO, $SO_2$ or O, and particularly X=S or $SO_2$. (compound 80, 81)

Another embodiment of the present invention relates to the compound of formula (III-11);characterized in that $R_{16}$= $C_{1-8}$ alkyl-halogen, particularly $R_{16}$=—$(CH_2)_2$—Br; X is S, SO, $SO_2$ or O, and particularly X=S or $SO_2$. (compound 64)

Another embodiment of the present invention relates to the compound of formula (III-11); characterized in that $R_{16}$ is (n = 0, 1 or 2)

particularly n=1. (compound 82)

Another embodiment of the present invention relates to the compound of formula (III-11);characterized in that $R_{15}$ and $R_{16}$ are independently selected from the group consisting of: $C_{1-8}$ alkyl, and particularly $R_{15}$=$R_{16}$=methyl; X is S, SO, $SO_2$ or O, and particularly X=S or $SO_2$. (compound 58)

Another embodiment of the present invention relates to the compound of formula (III), characterized in that X=S, structural format is as follows:

Formula (III-2)

Wherein:
$R_1$ is H, $NO_2$, $NR_{15}R_{16}$ or $CF_3$; $R_{15}$ and $R_{16}$ are independently selected from the group consisting of: H, $CH_3$ or ethanoyl;
$R_2$ is H, $NO_2$, $NR_{15}R_{16}$ or $CF_3$; $R_{15}$ and $R_{16}$ are independently selected from the group consisting of: H, $CH_3$ or ethanoyl; $R_1$ and $R_2$ cannot be H at same time;
$R_5$ is H, $NH_2$, $C_{1-8}$ alkyl or $C_{1-8}$ alkoxy;
$R_6$ is H, $NO_2$, $NH_2$ or $C_{1-8}$ alkoxy.

Another embodiment of the present invention relates to the compound of formula (III), characterized in that $R_1$=H, structural format is as follows:

Formula (III-21)

Wherein:
$R_2$ is H, $NO_2$, $NR_{15}R_{16}$ or $CF_3$; $R_{15}$ and $R_{16}$ are independently selected from the group consisting of: H, $CH_3$ or ethanoyl;
$R_5$ is H, $NH_2$, $C_{1-8}$ alkyl or $C_{1-8}$ alkoxy;
$R_6$ is H, $NO_2$, $NH_2$ or $C_{1-8}$ alkoxy.

Another embodiment of the present invention relates to the compound of formula (III-21), structural format is as follows:

Formula (III-21-1)

Another embodiment of the present invention relates to the compound of formula (III-21-1), characterized in that $R_2$ is $NR_{15}R_{16}$; $R_{15}$ and $R_{16}$ are independently selected from the group consisting of: H, $CH_3$ or ethanoyl; and particularly $R_2$=$NH_2$, $R_5$=methoxyl, $R_6$=$NO_2$. (compound 24, 27, 28, 29)

Another embodiment of the present invention relates to the compound of formula (III-2), characterized in that $R_1$=$NO_2$, $R_2$=H, structural format is as follows:

Formula (III-22)

Wherein:
$R_5$ is H, $NH_2$ or $C_{1-8}$ alkoxy;
$R_6$ is H, $NO_2$, $NH_2$ or $C_{1-8}$ alkoxy.

Another embodiment of the present invention relates to the compound of formula (III-2), characterized in that $R_5$ is 2-substituted or 4-substituted NH$_2$ or C$_{1-8}$ alkoxy, R$_6$ is 4-substituted NO$_2$, structural format is as follows:

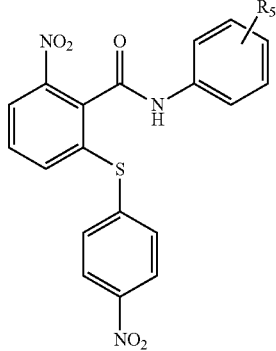

Formula (III-22-1)

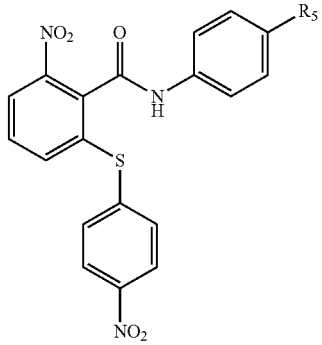

Formula (III-24)

Another embodiment of the present invention relates to the compound of formula (III-2-1), characterized in that R$_5$ is 2-substituted, structural format is as follows:

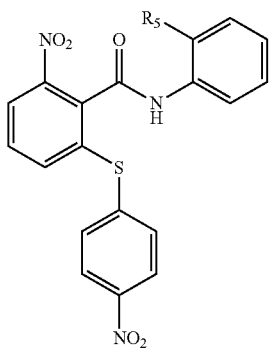

Formula (III-22-11)

wherein R$_5$ is C$_{1-8}$ alkoxy; and particularly R$_5$=methoxyl (compound 52) or R$_5$=NH$_2$. (compound 53)

Another embodiment of the present invention relates to the compound of formula (III-2), characterized in that R$_6$=NO$_2$, R$_5$=COOH. (compound 54) structural format is as follows:

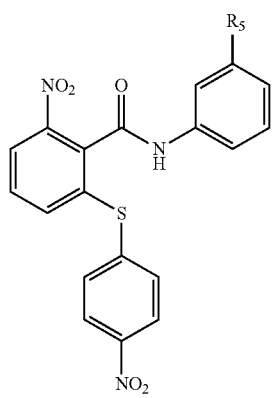

Formula (III-23)

Another embodiment of the present invention relates to the compound of formula (III-2), characterized in that R$_6$=NO$_2$, R$_5$=NH$_2$. (compound 55) structural format is as follows:

Another embodiment of the present invention relates to the compound of formula (III), characterized in that R$_1$=NH$_2$, R$_2$-R$_4$=H; R$_5$ is H, C$_{1-8}$ alkoxy, C$_{1-8}$ alkyl or NH$_2$; R$_6$ is H, NO$_2$, NH$_2$ or C$_{1-8}$ alkoxy.

Another embodiment of the present invention relates to the compound of formula (III); characterized when X=S; R$_1$ is H,

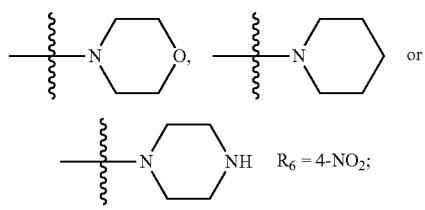

R$_6$ = 4-NO$_2$;

R$_5$=methoxyl; (compound 62, 63)
when X is O=S=O; R$_6$=4-NO$_2$; R$_5$=methoxyl.
Examples of formula compounds are shown below.

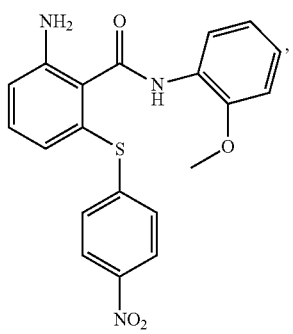

,

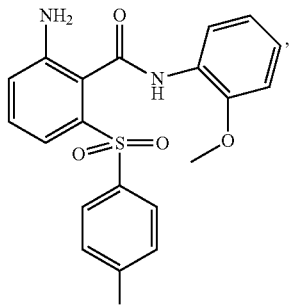

,

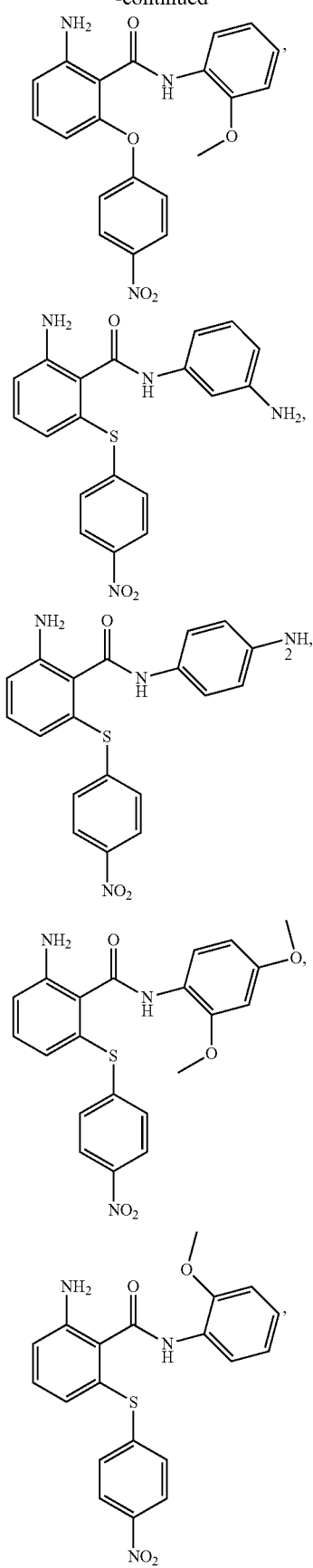

17
-continued
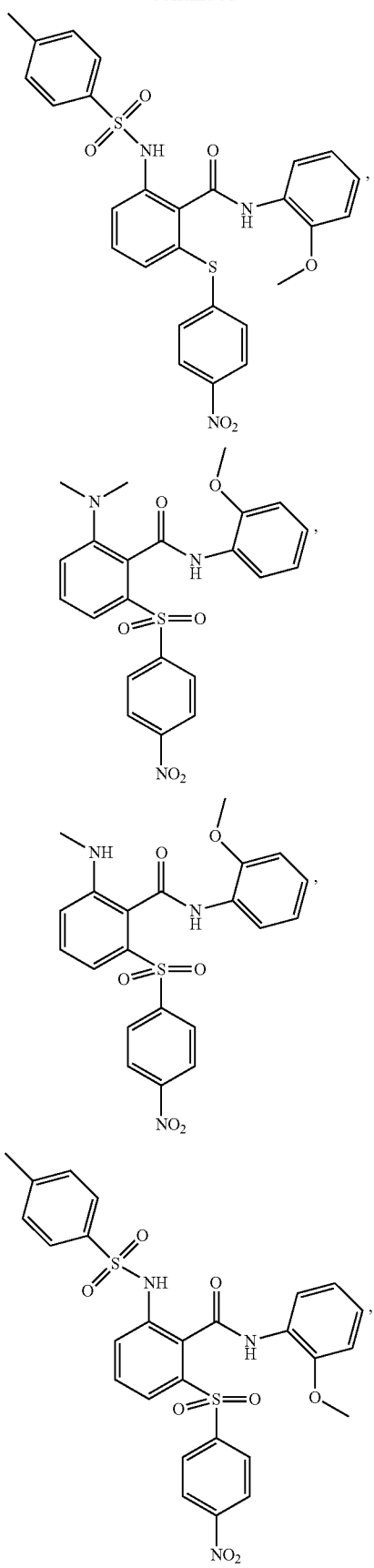
18
-continued
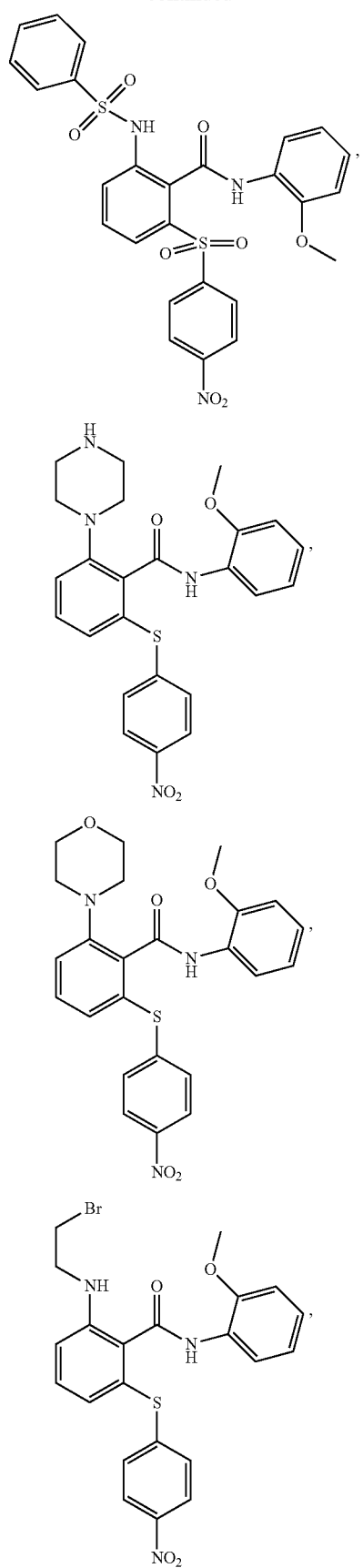

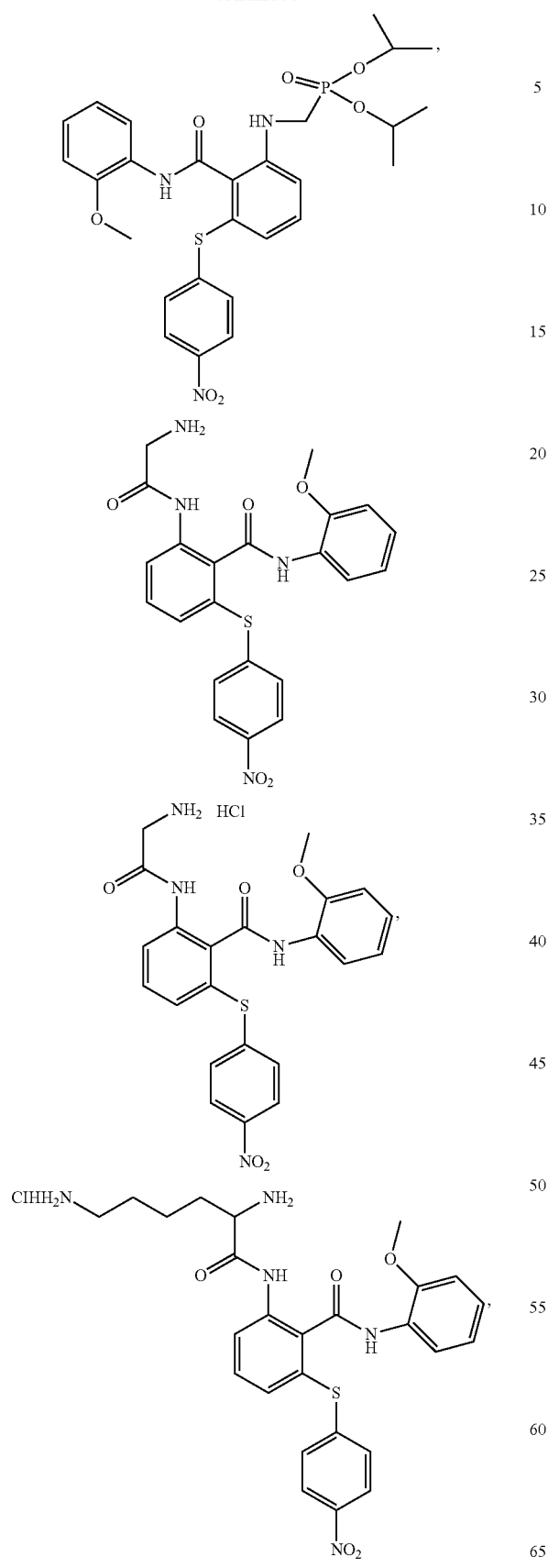
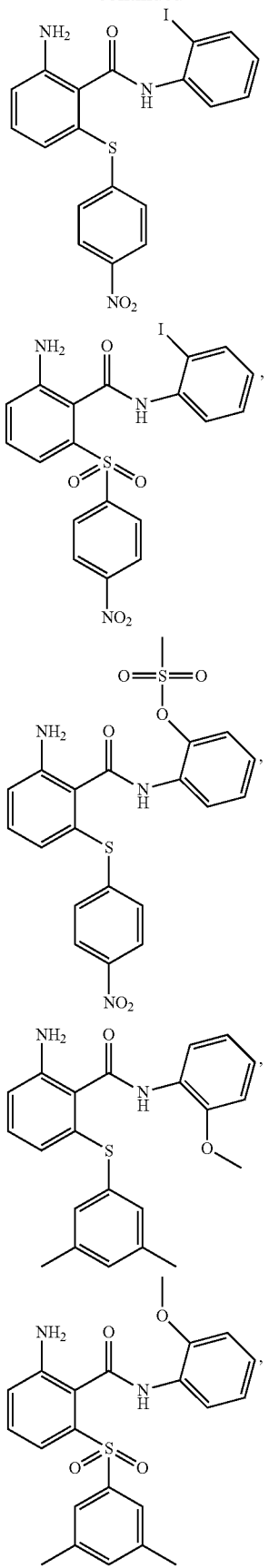

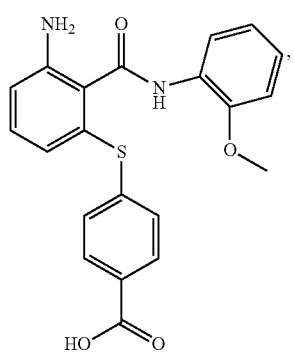
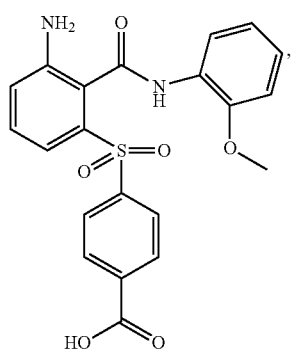
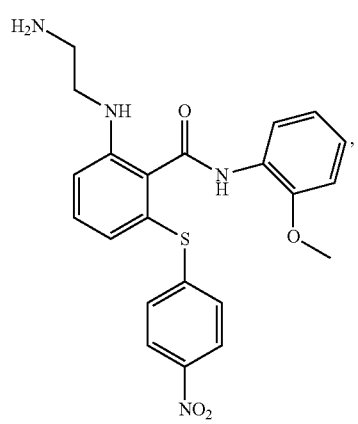
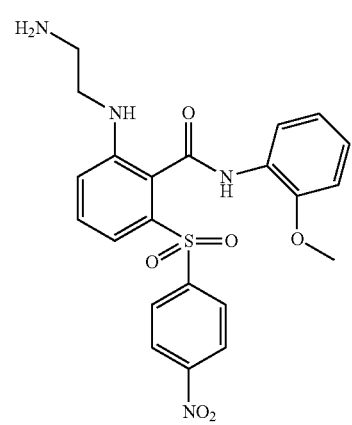
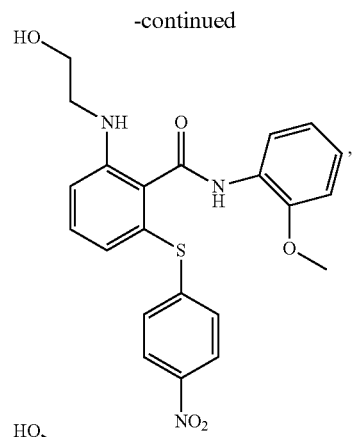
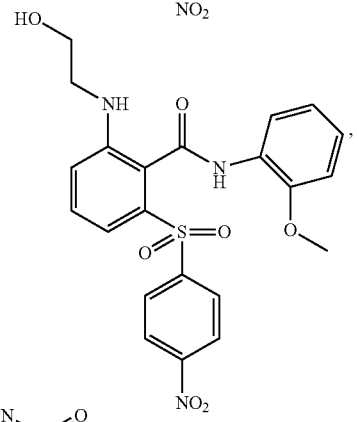
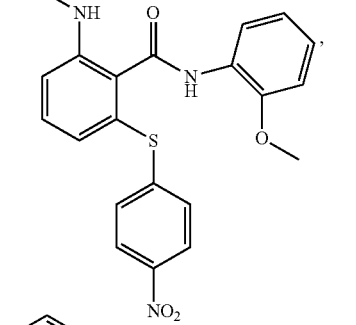, or
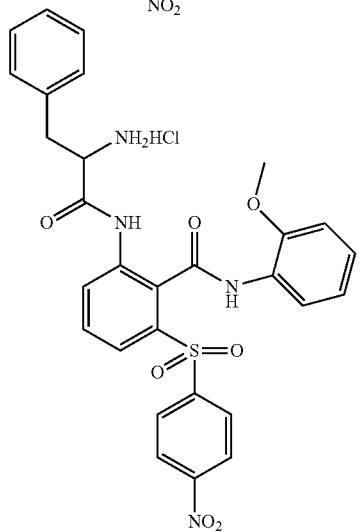

The present invention also provides for processes of making the pharmaceutically acceptable salts. The term "salts" as used herein refers to hydrochloride, sulfate, phosphate or nitrate and particularly hydrochloride.

The present invention also provides for compound's application as anti-HIV drug, antitumor drug or anti-HBV drug.

Moreover, the present invention also provides for compound's application as HIV-1 or HIV-2 inhibitor.

Formula I compounds of the present invention are prepared using the method described below:

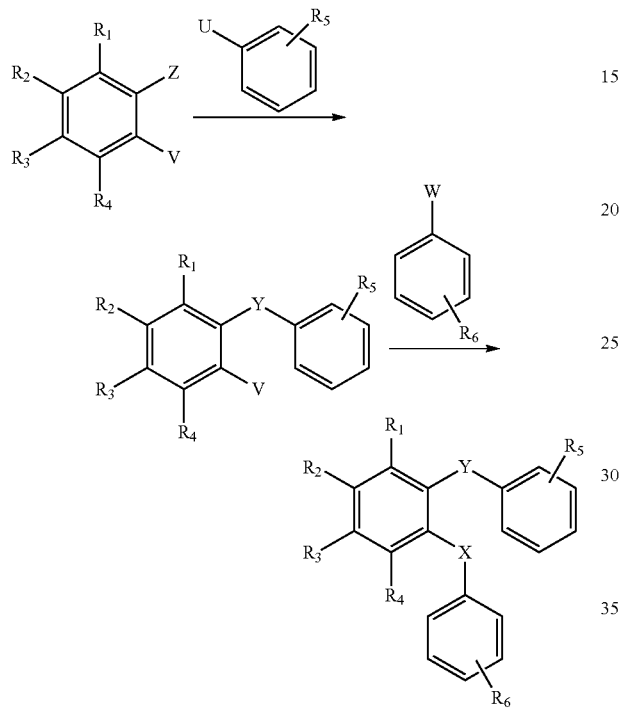

Wherein X=S, SO, SO$_2$ or O;
Y=CONR$_7$, NR$_7$CO, SO$_2$NR$_7$ or NR$_7$SO$_2$;
Z=COOH, COCl,

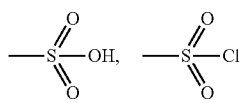

or NR$_7$H;
U=COOH, COCl,

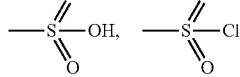

or NR$_7$H;
When Z=COOH, COCl,

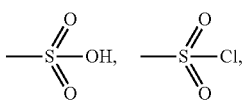

U=NR$_7$H; when U=COOH, COCl,

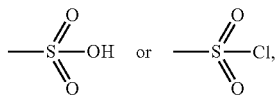

Z=NR$_7$H;
V=Cl, Br or I; W=SH or OH.
When X=S, the synthesis route are described below:

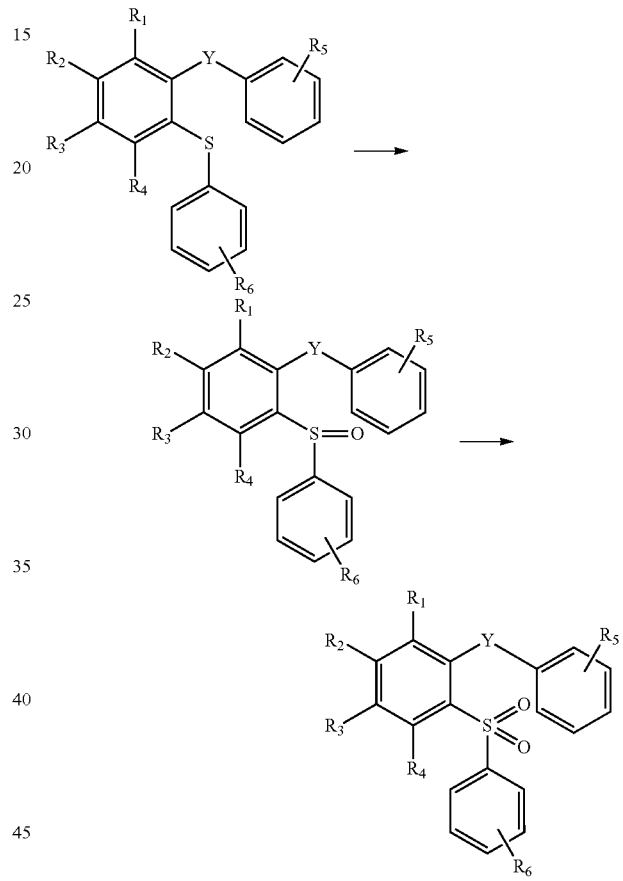

Wherein Y=CONR$_7$, NR$_7$CO, SO$_2$NR$_7$ or NR$_7$SO$_2$.

The beneficial effect of the invention:

The compounds have anti-HIV-1 and anti-HIV-2 virus activity, and have a C8166 therapeutic index as high as 2081.59 and an H9 therapeutic index as high as 303.03. Furthermore, the compounds have high solubility (1290-2845.5 μg/ml in an aqueous solution), and can be formulated into an oral formulation.

BRIEF DESCRIPTION OF THE DRAWINGS

The following detailed description, given by way of example, but not intended to limit the invention solely to the specific embodiments described, may best be understood in conjunction with the accompanying drawings, in which.

EXPERIMENTAL EXAMPLES

Example 1

Figure 1:
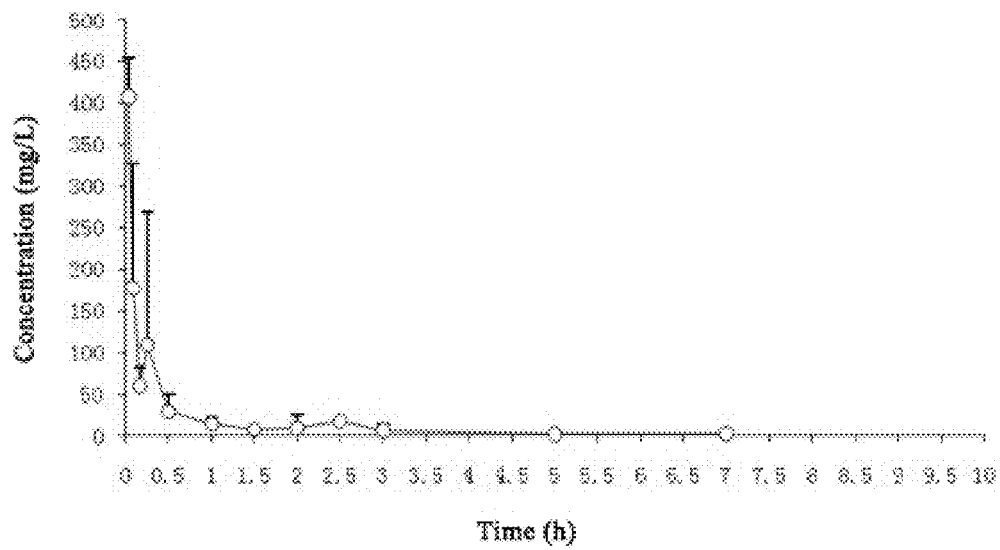
FIG. 1 shows a plasma concentration image of compound 67 at 100 mg/Kg by gavage.

General Procedure for 2-amino-N-(2-methoxyphenyl)-6-(4-nitrophenylthi-o)benzamide (Compound 25)

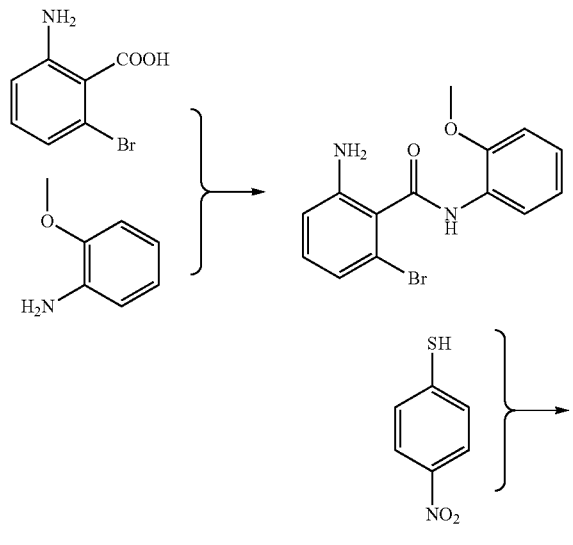

Synthesis of 2-amino-6-bromo-N-(2-methoxyphenyl)benzamide

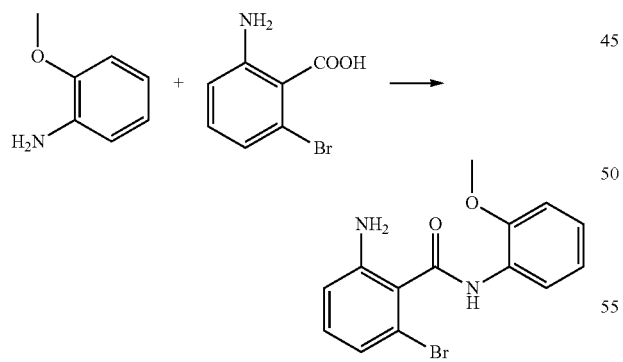

A mixture of 2-methoxyaniline (1.0 equiv.), 2-amino-6-bromobenzoic acid (1.0 equiv.), EDCI (1.2 equiv.) in THF (10 ml) was stirred at room temperature for 5 hrs. After the reaction was completed, the THF was removed by vacuum distillation. The resulting reaction mixture was extracted with EtOAc (3×20 mL). The combined organic extracts were washed with water (20 mL), brine (20 mL), dried over MgSO$_4$ and concentrated in vacuo. The residue was purified over silica gel using EtOAc:Hexanes (1:4) as the eluent to afford intermediate 25 (yield 85%) as a brown crystalline solid.

$^1$H NMR (400 MHz, DMSO) δ=3.80 (s, 3H), 5.33 (s, 2H), 6.72 (d, J=8 Hz, 1H), 6.78 (d, J=8 Hz, 1H), 6.99 (m, 2H), 6.07 (d, J=8.4 Hz, 1H), 7.18 (t, J=7.6 Hz, 1H), 7.85 (t, J=7.2 Hz, 1H), 9.43 (s, 1H).

ESI-MS: [M+Na]$^+$ m/z 346.

Synthesis of 2-amino-N-(2-methoxyphenyl)-6-(4-nitrophenylthi-o)benzamide

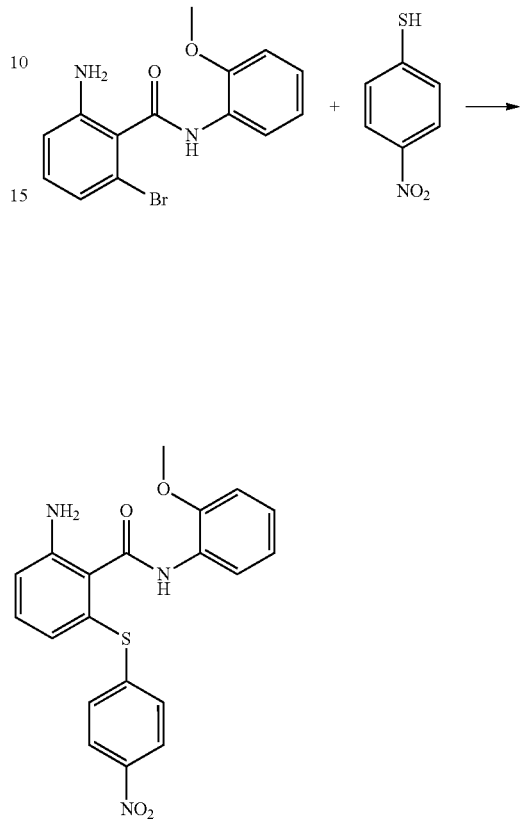

-continued

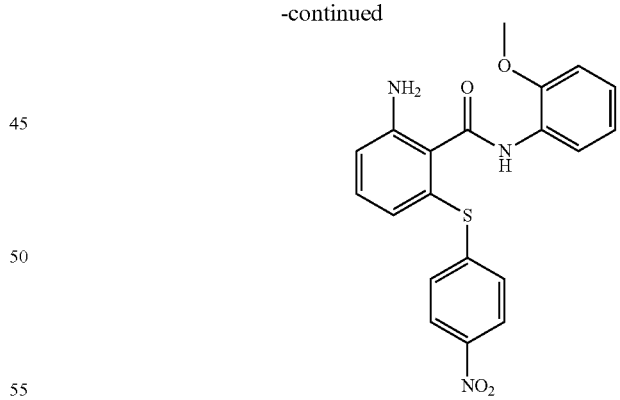

A mixture of 2-amino-6-bromo-N-(2-methoxyphenyl) benzamide (1.0 equiv.), 4-nitrobenzenethiol (2.0 equiv.), nanometer copper powder (0.5 equiv.) and anhydrous potassium carbonate (3.0 equiv.) were mixed in DMF (40 mL) at RT. Then the reaction flask was heated in an oil bath at 65° C. After 8 h, the heating bath was removed and the reaction flask was allowed to cool to room temperature. The reaction mixture was filtered and the liquid layer was diluted with water (40 mL), extracted with ethyl acetate (3×20 mL), washed with water (6×15 mL), dried over anhydrous Na$_2$SO$_4$, filtered, and concentrated under reduced pressure. The residue was purified by silica gel column chromatography (1:3 v/v ethyl acetate/petroleum ether) to provide the product compound 6 as a yellow amorphous solid (yield 75%).

$^1$H NMR (400 MHz, CDCl$_3$) δ=3.69 (s, 3H), 4.54 (br, 2H), 6.84 (d, J=8 Hz, 2H), 6.95 (m, 2H), 7.06 (t, J=8 Hz, 1H), 7.22 (m, 3H), 8.03 (d, J=7.6 Hz, 2H), 8.23 (s, 1H), 8.32 (d, J=7.6 Hz, 1H).

ESI-MS: [M+H]$^+$ m/z 396.

Example 2

General Procedure for N-(2-methoxyphenyl)-2-((4-nitrophenyl)thio)-5-(trifluoromethyl)benzamide (Compound 22)

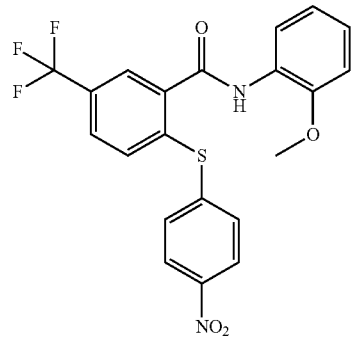 [SMILES: COc1ccccc1NC(=O)c1cc(C(F)(F)F)ccc1Sc1ccc([N+](=O)[O-])cc1]

Prepared by proceeding in similar manner to example 1, staring from N-(2-methoxyphenyl)-2-((4-nitrophenyl)thio)-5-(trifluoromethyl)benzamide. Yellow solid; 77.9% yield;

$^1$H NMR (400 MHz, CDCl$_3$) δ=3.85 (s, 3H), 6.90 (d, J=8.1 Hz, 1H), 6.99 (t, J=7.6 Hz, 1H), 7.11 (td, J=8.0, 1.5, 1H), 7.44 (d, J=8.8, 2H), 7.52 (d, J=8.3 Hz, 1H), 7.67 (dd, J=8.3, 1.5, 1H), 7.97 (s, 1H), 8.14 (t, J=5.7, 2H), 8.39 (d, J=6.2, 2H).

ESI-MS: [M+H]$^+$ m/z 449.

Example 3

General Procedure for N-(2-methoxyphenyl)-5-nitro-2-(4-nitrophenylthio)benzamide (Compound 23)

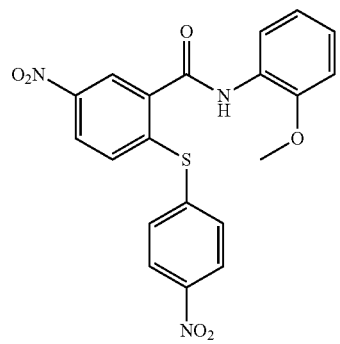 [SMILES: COc1ccccc1NC(=O)c1cc([N+](=O)[O-])ccc1Sc1ccc([N+](=O)[O-])cc1]

Prepared by proceeding in similar manner to example 1, staring from 2-bromo-5-nitrobenzoic acid. Yellow solid; 82.5% yield;

$^1$H NMR (400 MHz, CDCl$_3$) δ=3.80 (s, 3H), 6.88 (d, J=8 Hz, 1H), 6.92 (t, J=8 Hz, 1H), 7.03 (t, J=7.2 Hz, 1H), 7.16 (m, 2H), 7.34 (d, J=7.2 Hz, 1H), 7.68 (d, J=8 Hz, 1H), 7.89 (d, J=7.2 Hz, 1H), 8.12 (d, J=8 Hz, 2H), 8.43 (s, 1H), 8.57 (s, 1H) ppm.

ESI-MS: [M+Na]$^+$ m/z 448.

Example 4

General Procedure for 2-amino-N-(2-methoxyphenyl)-6-(4-nitrophenyl-thio)benzamide hydrochloride

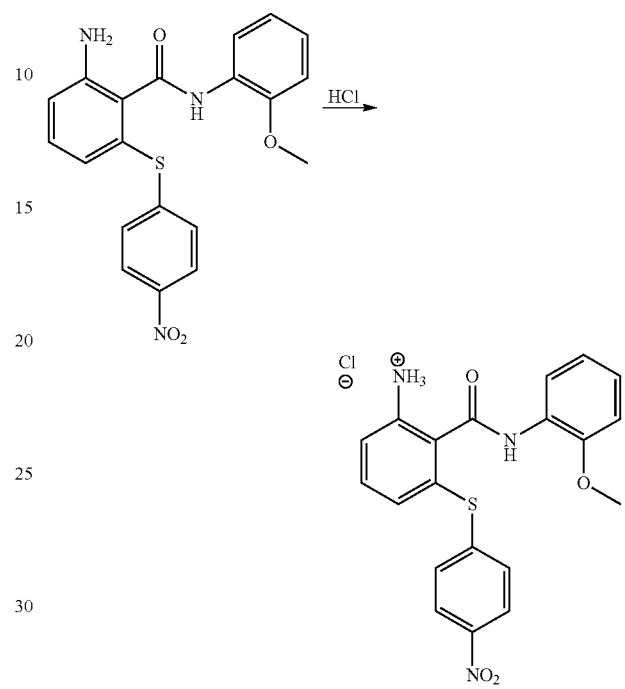

2-amino-N-(2-methoxyphenyl)-6-(4-nitrophenyl-thio)benzamide dissolved in EA, stirred at room temperature, while HCl is inlet till occurred to white solid. The reaction mixture was filtered to get White solid; 94.2% yield;

$^1$H NMR (400 MHz, DMSO) δ=3.69 (s, 3H), 5.33 (br, 3H), 6.81 (d, J=7.6 Hz, 1H), 6.92 (m, 2H), 7.01 (d, J=8 Hz, 1H), 7.12 (t, J=7.6 Hz, 1H), 7.25 (t, J=8 Hz, 1H), 7.31 (d, J=8.8 Hz, 2H), 7.758 (d, J=8 Hz, 1H), 8.098 (d, J=8.4 Hz, 2H), 9.397 (br, 1H) ppm.

ESI-MS: [M+Na]$^+$ m/z 403.

Example 5

General Procedure for 2-amino-N-(2-methoxyphenyl)-6-(4-nitrophenyl-thio)benzamide sulfate

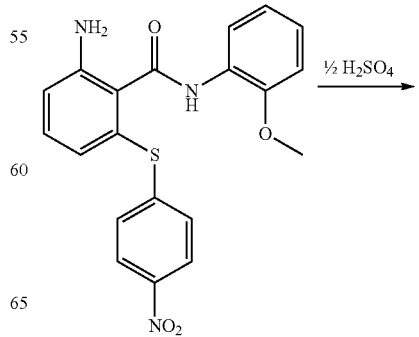

-continued

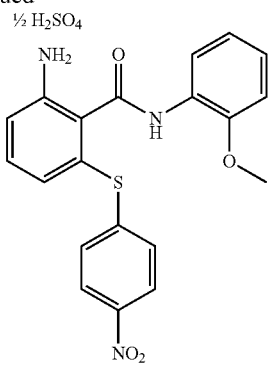

2-amino-N-(2-methoxyphenyl)-6-(4-nitrophenyl-thio) benzamide dissolved in EA, stirred at room temperature, while dropped H₂SO₄ into mixture till occurred to white solid. The reaction mixture was filtered to get White solid; 72% yield;

$^1$H NMR (400 MHz, DMSO) δ=3.69 (s, 3H), 4.02 (br, 3H), 6.78 (d, J=8.4 Hz, 1H), 6.90 (m, 2H), 7.01 (d, J=7.6 Hz, 1H), 7.10 (t, J=7.6 Hz, 1H), 7.236 (t, J=8 Hz, 1H), 7.305 (d, J=8.8 Hz, 2H), 7.753 (d, J=7.6 Hz, 1H), 8.097 (d, J=8.8 Hz, 2H), 9.379 (br, 1H) ppm.

ESI-MS: [M+Na]⁺ m/z 448.

Example 6

General Procedure for 2-amino-N-(2-methoxyphenyl)-6-((4-nitrophen-yl)sulfinyl)benzamide

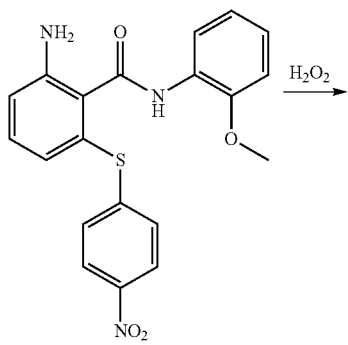

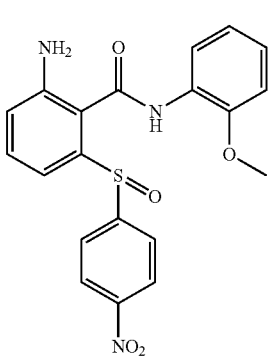

Compound 25 (1.0 equiv.) was dissolved in CH₃OH (30 mL) with a magnetic stirrer at RT, and 35% H₂O₂ (3.0 equiv.) was added slowly to this solution. This reaction mixture was heated in an oil bath at 66° C. and monitored using TLC. The reaction was quenched with MnO₂ at RT. The mixture was filtered and the residue was washed with ethyl acetate (3×5 mL). The liquid layer was concentrated under reduced pressure and the oily residue was purified by silica gel column chromatography (1:4 v/v ethyl acetate/petroleum ether) to provide a yellow solid; 44.3% yield;

$^1$H NMR (400 MHz, CDCl₃) δ=3.90 (s, 3H), 4.46 (brs, 2H), 6.88 (d, J=8.0 Hz, 1H), 6.96 (d, J=8.0 Hz, 1H), 7.04 (t, J=7.6 Hz, 1H), 7.17 (t, J=8.0 Hz, 1H), 7.41 (t, J=8.0 Hz, 1H), 7.47 (d, J=7.2 Hz, 1H), 7.91 (d, J=8.8 Hz, 2H), 8.21 (d, J=8.8 Hz, 2H), 8.28 (d, J=7.2 Hz, 1H), 8.75 (brs, 1H).

ESI-MS: [M+Na]⁺ m/z 434.

Example 7

General Procedure for 2-amino-N-(2-methoxyphenyl)-6-((4-nitroph-enyl)sulfonyl)benzamide (Compound 46)

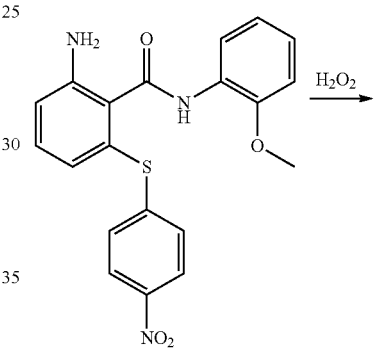

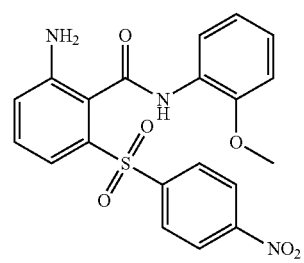

Compound 25 (1.0 equiv.) was dissolved in acetic acid (30 mL) with a magnetic stirrer at RT, and H₂O₂ (3.0 equiv.) was added to this solution. This reaction mixture was heated in an oil bath at 65° C. and the reaction was monitored using TLC. The reaction was quenched with MnO2 (3.5 equiv.) at RT. The mixture was filtered and the residue was washed with ethyl acetate (3×10 mL). The liquid layer was concentrated under reduced pressure and the oily residue was purified by silica gel column chromatography (1:2 v/v ethyl acetate/petroleum ether) to provide the product as a yellow amorphous solid (162.4 mg, 38% yield).

$^1$H NMR (400 MHz, DMSO) δ=3.79 (s, 3H), 5.57 (s, 2H), 7.01 (t, J=7.6 Hz, 1H), 7.08 (m, 2H), 7.22 (t, J=7.6 Hz, 1H), 7.29 (d, J=7.6 Hz, 1H), 7.36 (t, J=7.6 Hz, 1H), 7.76 (d, J=7.6 Hz, 1H), 8.16 (d, J=8.8 Hz, 2H), 8.36 (d, J=8.8 Hz, 2H), 9.71 (s, 1H).

ESI-MS: [M+H]⁺ m/z 428.

Example 8

General Procedure for 5-amino-N-(2-methoxyphenyl)-2-((4-nitrophenyl)thio)benzamide (Compound 24)

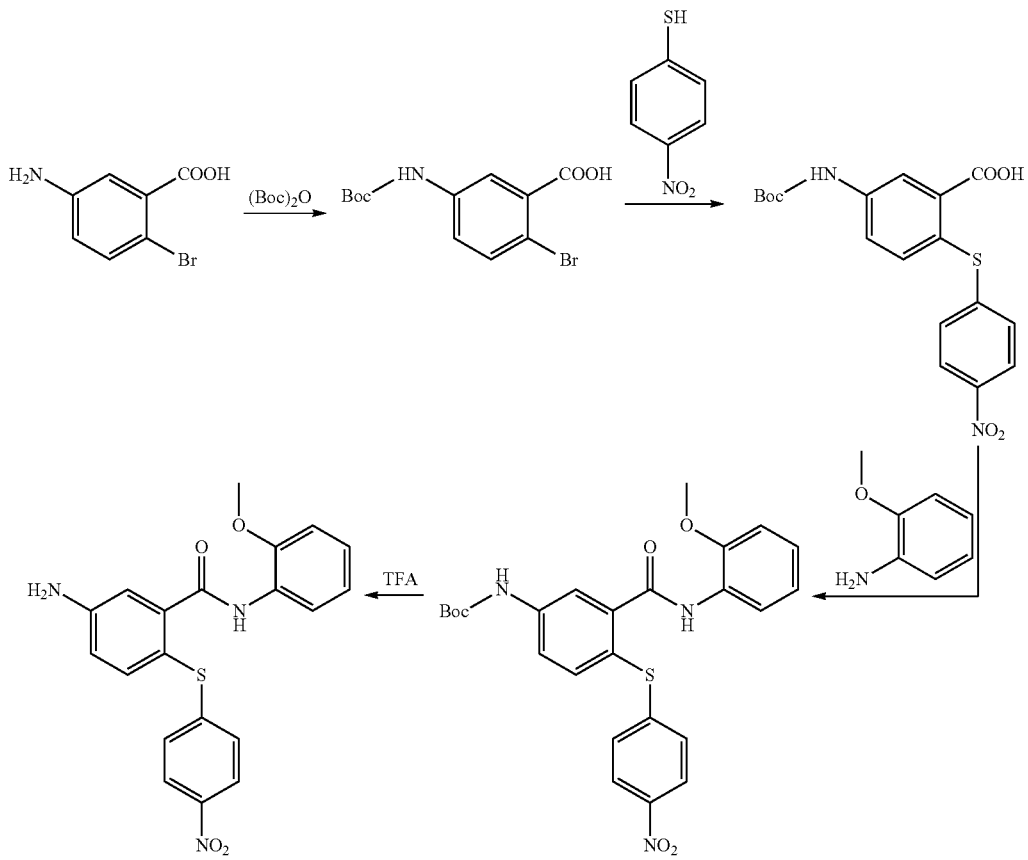

Intermediate 8a

Synthesis of 2-bromo-5-(tert-butoxycarbonylamino)benzoic acid

A mixture of 2-bromo-5-aminobenzoate (1.0 equiv.), BOC anhydride (1 equiv.) was dissolved in 15 mL THF, and stirring at room temperature, and DMAP (0.5 equiv.) was added to this solution, then dropped triethylamine (2.0 equiv.) to the mixture. The reaction stirring continued for 5 hours at room temperature. After the reaction was complete, the reaction solution was concentrated under reduced pressure, concentrate was dissolved in ethyl acetate, the organic layer was washed once with saturated brine, dried over anhydrous $Na_2SO_4$, purified by column chromatography (petroleum ether:ethyl acetate) to give a yellow solid 8a, in 95% yield.

Intermediate 8b

Synthesis of 5-(tert-butoxycarbonylamino)-2-(4-nitrophenyl-thio)benzoic acid A mixture of intermediate 8a (1.0 equiv.), 4-nitrobenzenethiol (2.0 equiv.), nanometer copper powder (0.5 equiv.) and anhydrous potassium carbonate (3.0 equiv.) were mixed in DMF (40 mL) at RT. Then the reaction flask was heated in an oil bath at 55° C. After 8 h, the heating bath was removed and the reaction flask was allowed to cool to room temperature. The reaction mixture was filtered and the liquid layer was diluted with water (40 mL), extracted with ethyl acetate (3×20 mL), washed with water (6×15 mL), dried over anhydrous $Na_2SO_4$, filtered, and concentrated under reduced pressure. The residue was purified by silica gel column chromatography (1:3 v/v ethyl acetate/petroleum ether) to provide the product intermediate 8b as a yellow amorphous solid; 77% yield.

Intermediate 8c

Synthesis of tert-butyl 3-(2-methoxyphenylcarbamoyl)-4-(4-nitrophenylthio)phenylcarbamate A mixture of 2-methoxyaniline(1.0 equiv.), intermediate 8b (1.0 equiv.), EDCI (1.2 equiv.) in DCM (10 ml) was stirred at room temperature for 5 hrs. After the reaction was completed, the DCM was removed by vacuum distillation. The resulting reaction mixture was extracted with EtOAc (3×20 mL). The combined organic extracts were washed with water (20 mL), brine (20 mL), dried over MgSO4 and concentrated in vacuo. The residue was purified over silica gel using EtOAc:Hexanes (1:4) as the eluent to afford intermediate 8c (yield 79%) as a white solid.

Synthesis of 5-amino-N-(2-methoxyphenyl)-2-(4-nitrophenylthio)benzamide

The 8c (1.0 equiv.) was dissolved in DCM, stirring at room temperature, dropwise trifluoroacetic acid (TFA 5 mmol) into the mixture, then stirred for 2 hours at room temperature. After completion of the reaction, the reaction solution was concentrated under reduced pressure, concentrate was dissolved in ethyl acetate, the organic layer was washed once with saturated brine, dried over anhydrous sodium sulfate and then was added, and finally the organic layer was concentrated under reduced pressure, purified by column chromatography (petroleum ether:ethyl acetate) to give a yellow solid, yield 84%.

$^1$H NMR (400 MHz, CDCl$_3$) δ=3.71 (s, 3H), 4.20 (brs, 2H), 6.82 (m, 2H), 6.95 (t, J=7.6 Hz, 1H), 7.04 (t, J=8.0 Hz, 1H), 7.14 (m, 3H), 7.42 (d, J=8.0 Hz, 1H), 8.03 (d, J=9.2 Hz, 2H), 8.40 (d, J=8.0 Hz, 1H), 8.45 (brs, 1H).

ESI-MS: [M+H]$^+$ m/z 396.

Example 9

General Procedure for N-(2-methoxyphenyl)-5-(methylamino)-2-((4-nitrophenyl)thio)benzamide (Compound 27)

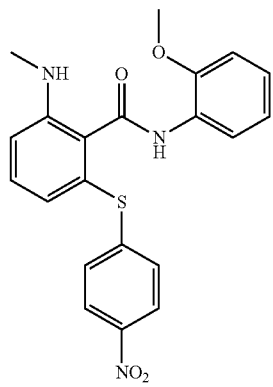 [SMILES: CNc1cccc(Sc2ccc([N+](=O)[O-])cc2)c1C(=O)Nc1ccccc1OC]

Compound 24 (1.0 equiv.) was dissolved in DMF (40 mL) and treated with anhydrous potassium carbonate (2.0 equiv.) at room temperature. To this mixture was added iodomethane (0.9 equiv.) via a micro syringe. After being stirred for 10 h at 50° C., the reaction mixture was poured into ice-cold water (200 mL) to get crude product. The crude solid was filtered and washed several times with water and purified by silica gel column chromatography (1:6 v/v ethyl acetate/petroleum ether) to provide a yellow solid (43% yield).

$^1$H NMR (400 MHz, CDCl$_3$) δ=2.93 (s, 3H), 3.69 (s, 3H), 4.24 (brs, 1H), 7.72 (d, J=8.4 Hz, 1H), 6.82 (d, J=8.0 Hz, 1H), 6.94 (t, J=6.4 Hz, 1H), 7.03 (m, 2H), 7.13 (d, J=8.8 Hz, 2H), 7.43 (d, J=8.4 Hz, 1H), 8.02 (d, J=8.8 Hz, 2H), 8.41 (d, J=8.0 Hz, 1H), 8.45 (brs, 1H).

ESI-MS: [M+H]$^+$ m/z 410.

Example 10

General Procedure for 5-(dimethylamino)-N-(2-methoxyphenyl)-2-((4-nitrophenyl)thio)benzamide (Compound 28)

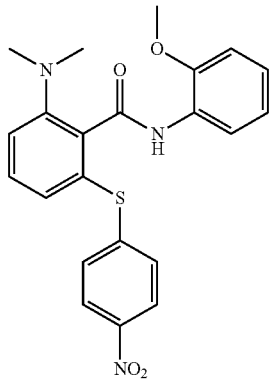 [SMILES: COc1ccccc1NC(=O)c1c(Sc2ccc([N+](=O)[O-])cc2)cccc1N(C)C]

Compound 24 (1.0 equiv.) was dissolved in DMF (40 mL) and treated with anhydrous potassium carbonate (4.0 equiv.) at room temperature. To this mixture was added iodomethane (2.5 equiv.) via a micro syringe. After being stirred for 10 Hours at 60° C., the reaction mixture was poured into ice-cold water (200 mL) to get crude product. The crude solid was filtered and washed several times with water and purified by silica gel column chromatography (1:8 v/v ethyl acetate/petroleum ether) to provide a yellow solid (78.1% yield).

1H NMR (400 MHz, CDCl$_3$) δ=3.09 (s, 6H), 3.69 (s, 3H), 6.83 (m, 2H), 6.95 (t, J=6.8 Hz, 1H), 7.04 (t, J=7.6 Hz, 1H), 7.13 (m, 3H), 7.47 (d, J=8.4 Hz, 1H), 8.03 (d, J=9.2 Hz, 2H), 8.43 (dd, J=8.0, 1.2 Hz, 1H), 8.48 (brs, 1H).

ESI-MS: [M+H]$^+$ m/z 424.

Example 11

General Procedure for 5-acetamido-N-(2-methoxyphenyl)-2-((4-nitrophenyl)thio)benzamide (Compound 29)

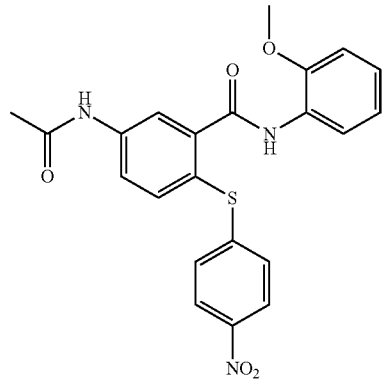 [SMILES: COc1ccccc1NC(=O)c1cc(NC(C)=O)ccc1Sc1ccc([N+](=O)[O-])cc1]

Compound 24 (1.0 equiv.) was dissolved in DCM (30 mL) at room temperature. To this mixture was added acetic anhydride (1.2 equiv.), followed by the addition of DMAP (0.5 equiv.). After being stirred for 5 hours at room temperature, the reaction mixture was concentrated under reduced pressure. The crude residue was diluted ethyl acetate (60 mL), washed with water (2×15 mL), dried over anhydrous Na$_2$SO$_4$, filtered, and concentrated under reduced pressure. The residue was purified by silica gel column chromatography (1:6 v/v ethyl acetate/petroleum ether) to provide a yellow solid; 96% yield;

¹H NMR (400 MHz, CDCl₃) δ=2.18 (s, 3H), 3.73 (s, 3H), 6.85 (d, J=8.4 Hz, 1H), 6.95 (t, J=7.6 Hz, 1H), 7.07 (t, J=8.0 Hz, 1H), 7.19 (d, J=8.8 Hz, 2H), 7.56 (d, J=8.8 Hz, 1H), 7.83 (d, J=1.6 Hz, 1H), 7.94 (d, J=8.0 Hz, 1H), 7.98 (br, 1H), 8.04 (d, J=9.2 Hz, 2H), 8.35 (d, J=7.6 Hz, 1H), 8.51 (br, 1H) ppm.
ESI-MS: [M+H]⁺ m/z 438.

Example 12

General Procedure for 2-amino-N-(2-methoxyphenyl)-6-(4-nitrop-henoxy)benzamide (Compound 48)

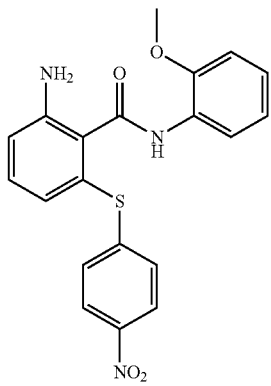 [SMILES: COc1ccccc1NC(=O)c1c(N)cccc1Sc1ccc([N+](=O)[O-])cc1]

Prepared by proceeding in similar manner to example 1, use 4-Nitrophenol instead of 4-nitrothiophenol. Yellow solid; 38% yield;
¹H NMR (400 MHz, CDCl₃) δ=3.77 (s, 3 H), 5.88 (br, 2 H), 6.28 (d, J=8 Hz, 1 H), 6.60 (d, J=8 Hz, 1 H), 6.90 (m, 2 H), 7.67 (t, J=8 Hz, 1 H), 7.00 (d, J=8 Hz, 2 H), 7.18 (t, J=8 Hz, 1 H), 8.21 (d, J=8.8 Hz, 2 H), 8.42 (d, J=8 Hz, 1 H), 9.49 (s, 1 H) ppm.
ESI-MS: [M+Na]⁻ m/z 402.

Example 13

General Procedure for 2-amino-N-(3-aminophenyl)-6-(4-nitroph-enylthio)benzamide (Compound 49)

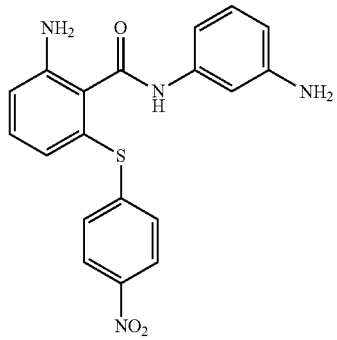 [SMILES: Nc1cccc(NC(=O)c2c(N)cccc2Sc2ccc([N+](=O)[O-])cc2)c1]

Prepared by proceeding in similar manner to example 1, use m-phenylenediamine instead of o-anisidine. Yellow solid; 38% yield;
¹H NMR (400 MHz, CDCl₃) δ=3.62 (br, 2 H), 5.78 (br, 2 H), 6.31 (d, J=8.4 Hz, 1 H), 6.62 (d, J=7.6 Hz, 1 H), 7.01 (m, 1 H), 7.45 (d, J=8 Hz, 2 H), 7.48 (m, 2 H), 7.82 (d, J=8 Hz, 1 H), 7.93 (d, J=8.8 Hz, 2 H), 8.01 (d, J=7.2 Hz, 1 H), 8.52 (s, 1H) ppm.
ESI-MS: [M+K]⁺ m/z 418.

Example 14

General Procedure for 2-amino-N-(4-amino-2-methoxyphenyl)-6-(4-nitrophenylthio)benzamide (Compound 50)

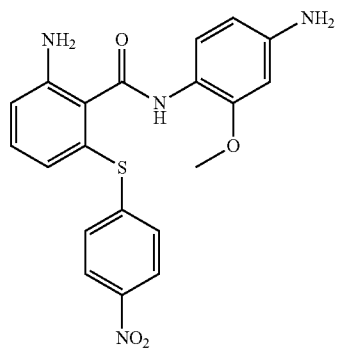 [SMILES: COc1cc(N)ccc1NC(=O)c1c(N)cccc1Sc1ccc([N+](=O)[O-])cc1]

Prepared by proceeding in similar manner to example 1, use 2-methoxybenzene-1,4-diamine instead of o-anisidine. Yellow solid; 69.8% yield;
1H NMR (400 MHz, CDCl₃) δ=3.82 (s, 3 H), 5.66 (br, 2 H), 6.42 (d, J=8 Hz, 2 H), 6.67 (t, J=7.2 Hz, 2 H), 7.12 (t, J=8 Hz, 1 H), 7.56 (m, 4 H), 8.00 (s, 1 H), 8.33 (d, J=8 Hz, 1 H), 8.92 (br, 2 H) ppm.
ESI-MS: [M+H]⁺ m/z 411.

Example 15

General Procedure for 2-amino-N-(2,4-dimethoxyphenyl)-6-(4-nitrophenylthio)benzamide (Compound 51)

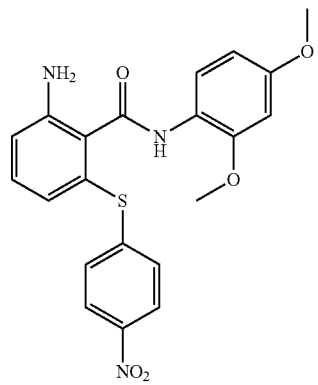 [SMILES: COc1ccc(NC(=O)c2c(N)cccc2Sc2ccc([N+](=O)[O-])cc2)c(OC)c1]

Prepared by proceeding in similar manner to example 1, use 2,4-dimethoxyaniline instead of o-anisidine. 61% yield;
1H NMR (400 MHz, CDCl₃) δ=3.82 (s, 3 H), 3.84 (s, 3 H), 6.52 (d, J=9.6 Hz, 2 H), 6.69 (t, J=9.2 Hz, 2 H), 7.08 (t, J=8 Hz, 1 H), 7.65 (m, 4 H), 8.15 (s, 1 H), 8.29 (d, J=8.8 Hz, 1 H), 9.05 (br, 2 H) ppm.
ESI-MS: [M+K]⁻ m/z 474.

Example 16

General Procedure for N-(2-methoxyphenyl)-2-nitro-6-(4-nitrophenylthio)benzamide (Compound 52)

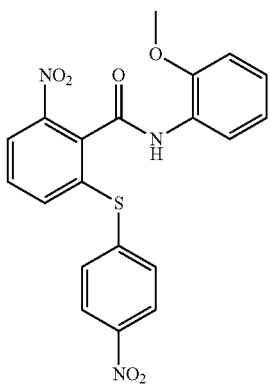 [SMILES: COc1ccccc1NC(=O)c1c(Sc2ccc([N+](=O)[O-])cc2)cccc1[N+](=O)[O-]]

Prepared by proceeding in similar manner to example 1, use 2-bromo-6-nitrobenzoic acid instead of 2-amino-6-bromobenzoic acid. 77% yield;

$^1$H NMR (400 MHz, CDCl$_3$) δ=3.73 (s, 3 H), 6.85 (d, J=7.2 Hz, 1 H), 7.00 (t, J=8 Hz, 1 H), 7.10 (t, J=8.8 Hz, 1 H), 7.30 (d, J=8.8 Hz, 2 H), 7.66 (t, J=8 Hz, 1 H), 7.85 (d, J=8.8 Hz, 2 H), 8.09 (d, J=9.2 Hz, 2 H), 8.28 (d, J=7.2 Hz, 1 H), 6.85 (d, J=7.2 Hz, 1 H) ppm.

ESI-MS: [M+K]$^-$ m/z 474.

Example 17

General Procedure for N-(2-aminophenyl)-2-nitro-6-(4-nitrophenylthio)benzamide (Compound 53)

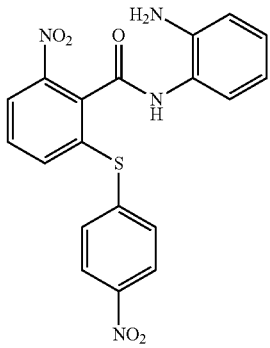 [SMILES: Nc1ccccc1NC(=O)c1c(Sc2ccc([N+](=O)[O-])cc2)cccc1[N+](=O)[O-]]

Prepared by proceeding in similar manner to example 16, use o-Phenylenediamine instead of o-anisidine. 68.5% yield;

$^1$H NMR (400 MHz, CDCl$_3$) δ=3.57 (br, 2 H), 6.83 (d, J=8 Hz, 2 H), 7.14 (t, J=7.2 Hz, 1 H), 7.22 (d, J=8 Hz, 2 H), 7.40 (d, J=8 Hz, 2 H), 7.68 (t, J=7.6 Hz, 1 H), 7.85 (d, J=8 Hz, 1 H), 7.09 (d, J=8 Hz, 2 H), 8.31 (d, J=8 Hz, 1 H) ppm.

ESI-MS: [M+H] m/z 411.

Example 18

General Procedure for 3-(2-nitro-6-(4-nitrophenylthio)benzamildo)benzoic acid (Compound 54)

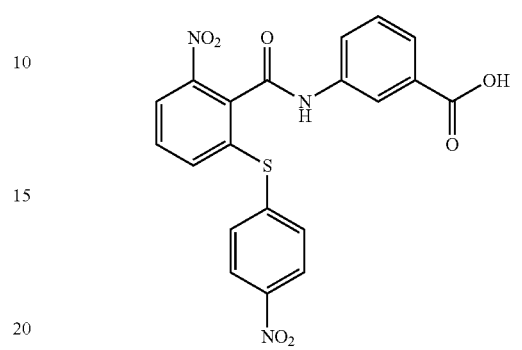

Prepared by proceeding in similar manner to example 16, use 3-aminobenzoic acid instead of o-anisidine. 43.1% yield;

$^1$H NMR (400 MHz, DMSO) δ=7.43 (d, J=8.8 Hz, 2 H), 7.48 (d, J=8 Hz, 1 H), 7.71 (m, 2 H), 7.84 (t, J=8 Hz, 1 H), 8.03 (d, J=8 Hz, 1 H), 8.15 (d, J=8.8 Hz, 2 H), 8.21 (s, 1 H), 8.39 (d, J=8 Hz, 1 H), 10.89 (s, 1 H), 13.04 (br, 1 H) ppm.

ESI-MS: [M−H]$^-$ m/z 438.

Example 19

General Procedure for N-(4-aminophenyl)-2-nitro-6-(4-nitrophenylthio)benzamide (Compound 58)

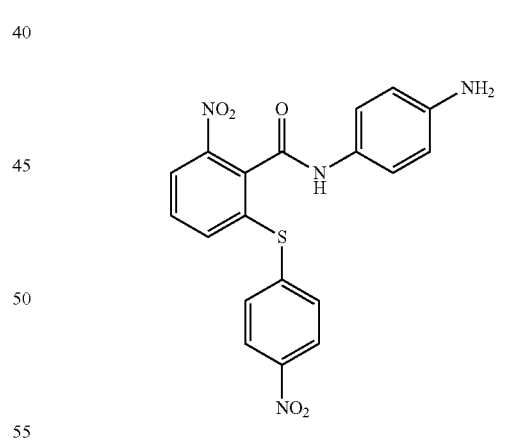

Prepared by proceeding in similar manner to example 16, use p-phenylenediamine instead of o-anisidine. 43.1% yield;

$^1$H NMR (400 MHz, CDCl$_3$) δ=3.72 (br, 2 H), 6.66 (d, J=8 Hz, 1 H), 6.71 (d, J=8.4 Hz, 2 H), 7.25 (m, 1 H), 7.37 (d, J=8.8 Hz, 2 H), 7.47 (t, J=8 Hz, 1 H), 7.61 (t, J=8.8 Hz, 1 H), 7.80 (d, J=8 Hz, 1 H), 7.94 (d, J=8 Hz, 1 H), 7.11 (d, J=9.2 Hz, 1 H), 8.17 (d, J=8 Hz, 1 H) ppm.

ESI-MS: [M+H]$^+$ m/z 411.

Example 20

General Procedure for N-(2-methoxyphenyl)-2-(4-nitrophenylthio)-6-(phenylsulfonamido)benzamide (Compound 56)

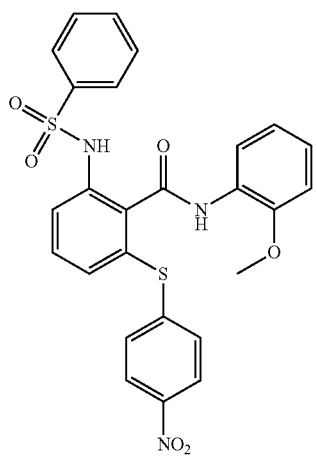 [SMILES: COc1ccccc1NC(=O)c1c(NS(=O)(=O)c2ccccc2)cccc1Sc1ccc([N+](=O)[O-])cc1]

Compound 25 (1.0 equiv.) was dissolved in azabenzene (40 mL) at room temperature. To this mixture was added benzenesulfonyl chloride (1.2 equiv.). After being stirred for 10 Hours at room temperature, the reaction mixture was concentrated under reduced pressure. The crude residue was diluted ethyl acetate (50 mL), washed with water (3×20 mL), dried over anhydrous $Na_2SO_4$, filtered, and concentrated under reduced pressure. The residue was purified by silica gel column chromatography (1:4 v/v ethyl acetate/petroleum ether) to provide a white solid. 67% yield;
$^1$H NMR (400 MHz, $CDCl_3$) δ=3.65 (s, 3H), 6.74 (d, J=8.0 Hz, 1H), 6.85 (t, J=7.6 Hz, 1H), 6.91 (d, J=8.0 Hz, 1H), 7.02 (t, J=7.6 Hz, 1H), 7.28 (m, 1H), 7.37 (t, J=8.0 Hz, 1H), 7.47 (t, J=7.6 Hz, 3H), 7.64 (m, 3H), 8.01 (m, 5H), 8.93 (s, 1H) ppm.
ESI-MS: [M+K]$^+$ m/z 558.

Example 21

General Procedure for N-(2-methoxyphenyl)-2-(4-methylphenylsulfonamido)-6-((4-nitrophenyl)thio)benzamide (Compound 57)

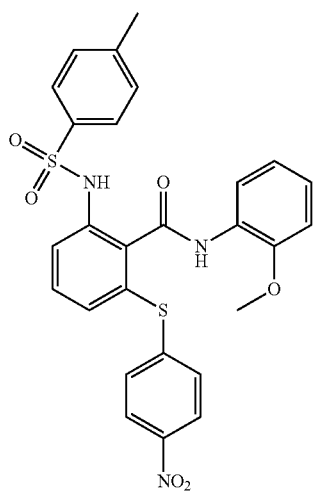 [SMILES: COc1ccccc1NC(=O)c1c(NS(=O)(=O)c2ccc(C)cc2)cccc1Sc1ccc([N+](=O)[O-])cc1]

Prepared by proceeding in similar manner to example 20, using Methyl-benzenesulfonyl chloride instead of benzenesulfonyl chloride. White solid; 83.8% yield;
$^1$H NMR (400 MHz, $CDCl_3$) δ=2.17 (s, 3H), 3.69 (s, 3H), 6.8 (d, J=8 Hz, 1H), 6.95 (d, J=8.8 Hz, 3H), 7.09 (m, 3H), 7.38 (d, J=8.0 Hz, 1H), 7.47 (t, J=8.0 Hz, 1H), 7.54 (d, J=8.0 Hz, 2H), 7.81 (d, J=8.0 Hz, 1H), 7.95 (s, 1H), 8.01 (d, J=8.8 Hz, 2H), 8.16 (d, J=8.0 Hz, 1H), 8.42 (s, 1H);
ESI-MS: [M+Na]$^+$ m/z 572.09

Example 22

General Procedure for 2-(dimethylamino)-N-(2-methoxyphenyl)-6-((4-nitrophenyl)sulfonyl)benzamide (Compound 58)

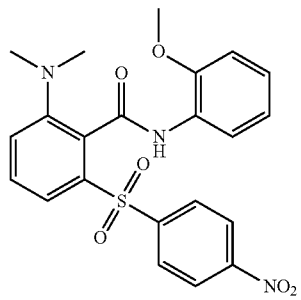 [SMILES: COc1ccccc1NC(=O)c1c(N(C)C)cccc1S(=O)(=O)c1ccc([N+](=O)[O-])cc1]

Prepared by proceeding in similar manner to example 7, using compound 28 instead of compound 25. Yellow solid; 77.2% yield;
$^1$H NMR (400MHz, $CDCl_3$) δ=2.76 (s, 3H), 3.28 (s, 3H), 4.08 (s, 3H), 6.61 (d, J=8.0 Hz, 1H), 7.09 (t, J=7.6 Hz, 1H), 7.13 (d, J=8.0 Hz, 1H), 7.21 (d, J=7.6 Hz, 2H), 7.36 (m, 2H), 7.43 (t, J=6.4 Hz, 1H), 7.60 (d, J=9.2 Hz, 2H), 7.91 (d, J=8.0 Hz, 2H);
ESI-MS: [M+Na]$^+$ m/z 478.10

Example 23

General Procedure for N-(2-methoxyphenyl)-2-(methylamino)-6-((4-nitrophenyl)sulfonyl)benzamide (Compound 59)

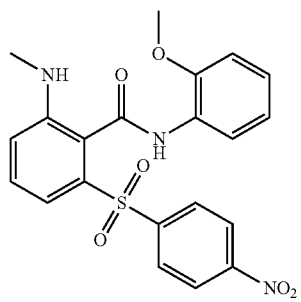 [SMILES: CNc1cccc(S(=O)(=O)c2ccc([N+](=O)[O-])cc2)c1C(=O)Nc1ccccc1OC]

Prepared by proceeding in similar manner to example 7, using compound 27 instead of compound 25. White solid; 85.2% yield;
$^1$H NMR (400 MHz, $CDCl_3$) δ=3.29 (s, 3H), 4.03 (s, 3H), 4.73 (brs, 1H), 7.21 (dd, J=8.0, 0.8 Hz, 1H), 7.04 (td, J=8.0, 1.2 Hz, 1H), 7.15 (dd, J=8.0, 1.2 Hz, 1H), 7.24 (m, 3H), 7.41 (m, 2H), 7.57 (m, 2H), 7.95 (d, J=12.0 Hz, 2H);
ESI-MS: [M+Na]$^+$ m/z 464.08

Example 24

General Procedure for N-(2-methoxyphenyl)-2-(4-methylphenyls-ulfonamido)-6-((4-nitrophenyl)sulfonyl)benzamide (Compound 60)

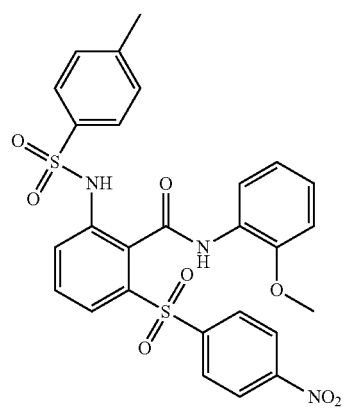 [SMILES: COc1ccccc1NC(=O)c1c(NS(=O)(=O)c2ccc(C)cc2)cccc1S(=O)(=O)c1ccc([N+](=O)[O-])cc1]

Prepared by proceeding in similar manner to example 7, using compound 57 instead of compound 25, White solid; 55% yield;

$^1$H NMR (400 MHz, CDCl$_3$) δ=2.17 (s, 3H), 3.64 (s, 3H), 6.77 (d, J=8.0 Hz, 1H), 6.95 (m, 2H), 7.09 (t, J=7.2 Hz, 1H), 7.19 (d, J=8.0 Hz, 1H), 7.42 (t, J=7.2 Hz, 2H), 7.61 (t, J=7.2 Hz, 1H), 7.81 (d, J=7.6 Hz, 1H), 7.95 (d, J=7.6 Hz, 2H), 8.10 (d, J=8.0 Hz, 1H), 8.26 (d, J=8.4 Hz, 2H), 8.33 (d, J=8.4 Hz, 2H), 9.18 (s, 1H);

ESI-MS: [M+Na]$^+$ m/z 604.08

Example 25

General Procedure for N-(2-methoxyphenyl)-2-((4-nitrophenyl)sulfonyl)-6-(phenylsulfonamido)benzamide (Compound 61)

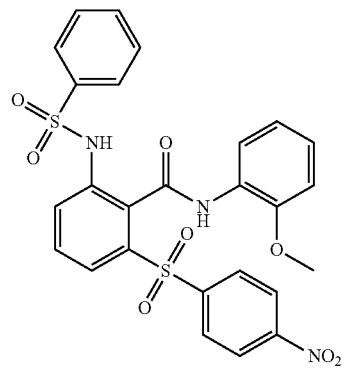 [SMILES: COc1ccccc1NC(=O)c1c(NS(=O)(=O)c2ccccc2)cccc1S(=O)(=O)c1ccc([N+](=O)[O-])cc1]

Prepared by proceeding in similar manner to example 7, using compound 56 instead of compound 25, White solid; 62% yield;

$^1$H NMR (400 MHz, CDCl$_3$) δ=3.64 (s, 3H), 6.77 (d, J=7.2 Hz, 1H), 6.95 (m, 2H), 7.09 (t, J=8.0 Hz, 1H), 7.44 (t, J=8.0 Hz, 2H), 7.49 (t, J=7.2 Hz, 1H), 7.61 (t, J=7.2 Hz, 2H), 7.95 (d, J=7.2 Hz, 3H), 8.10 (d, J=9.2 Hz, 1H), 8.27 (d, J=7.2 Hz, 2H), 8.32 (d, J=7.2 Hz, 2H), 9.18 (s, 1H);

ESI-MS: [M+Na]$^+$ m/z 590.06

Example 26

General Procedure for N-(2-methoxyphenyl)-2-((4-nitrophenyl)thio)-6-(piperazinyl)benzamide (Compound 62)

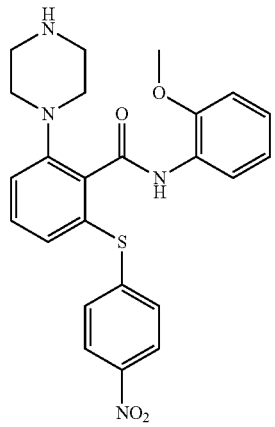 [SMILES: COc1ccccc1NC(=O)c1c(Sc2ccc([N+](=O)[O-])cc2)cccc1N1CCNCC1]

Compound 25 (1.0 equiv.) was dissolved in DMF (40 mL) at room temperature. To this mixture bis(2-bromoethyl)amine (1.0 equiv.) was added, following the addition of NaOH (2.0 equiv.). After being stirred for 2 Hours at room temperature, the reaction mixture was poured into ice-cold water (200 mL) to get crude product. The crude solid was filtered and washed several times with water and purified by silica gel column chromatography (1:3 v/v ethyl acetate/petroleum ether) to provide a yellow solid (380.9 mg, 82% yield).

$^1$H NMR (400 MHz, CDCl$_3$) δ=1.11 (s, 2H), 1.60 (s, 2H), 2.48 (t, J=4.8 Hz, 2H), 3.13 (t, J=6.0 Hz, 2H), 3.81 (s, 3H), 5.30 (s, 1H), 6.91 (d, J=8.0 Hz, 1H), 7.02 (d, J=8.0 Hz, 3H), 7.13 (t, J=7.6 Hz, 1H), 7.32 (m, 2H), 7.88 (s, 1H), 8.11 (d, J=8.8 Hz, 2H), 8.36 (d, J=8.0 Hz, 1H), 9.46 (s, 1H);

ESI-MS: [M+H]$^+$ m/z 465.16

Example 27

General Procedure for N-(2-methoxyphenyl)-2-morpholino-6-((4-nitrophenyl)thio)benzamide (Compound 63)

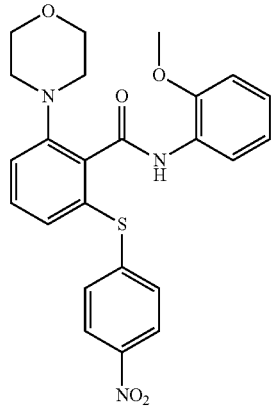 [SMILES: COc1ccccc1NC(=O)c1c(Sc2ccc([N+](=O)[O-])cc2)cccc1N1CCOCC1]

Prepared by proceeding in similar manner to example 26, using 2,2'-dibromodi-ethyl ether instead of bis(2-bromoethyl)amine, Yellow solid; 67% yield;

$^1$H NMR (400 MHz, CDCl$_3$) δ=1.33 (s, 2H), 1.74 (s, 2H), 2.55 (t, J=4.8 Hz, 2H), 3.21 (t, J=6.0 Hz, 2H), 3.82 (s, 3H), 7.02 (d, J=7.2 Hz, 1H), 7.12 (d, J=8.8 Hz, 3H), 7.23 (t, J=7.2 Hz, 1H), 7.32 (m, 2H), 7.91 (s, 1H), 8.22 (d, J=8.0 Hz, 2H), 8.32 (d, J=8.0 Hz, 1H), 9.46 (s, 1H);

ESI-MS: [M+H]⁺ m/z 466.14

Example 28

General Procedure for 2-((2-bromoethyl)amino)-N-(2-methoxyp-henyl)-6-((4-nitrophenyl)thio)benzamide (Compound 64)

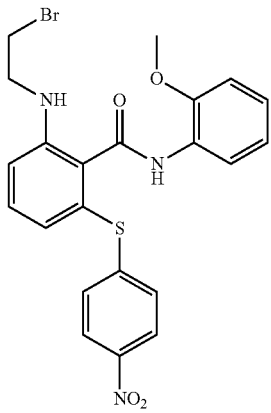 [SMILES: COc1ccccc1NC(=O)c1c(NCCBr)cccc1Sc1ccc([N+](=O)[O-])cc1]

Prepared by proceeding in similar manner to example 9, Yellow solid; 59.5% yield;

¹H NMR (400 MHz, CDCl₃) δ=3.27 (t, J=7.2 Hz, 2H), 3.45 (m, 2H), 3.87 (s, 3H), 4.14 (brs, 1H), 6.49 (d, J=9.2 Hz, 1H), 6.68 (d, J=4.0 Hz, 1H), 7.04 (m, 3H), 7.37 (m, 3H), 7.53 (t, J=4.0 Hz, 1H), 7.96 (d, J=8.0 Hz, 2H), 8.20 (s, 1H);

ESI-MS: [M+H]⁺ m/z 502.04

Example 29

General Procedure for diisopropyl(((2-((2-methoxyphenyl)carbamoyl)-3-((4-nitro-phenyl)thio)phenyl)amino)methyl)phosphonate (Compound 65)

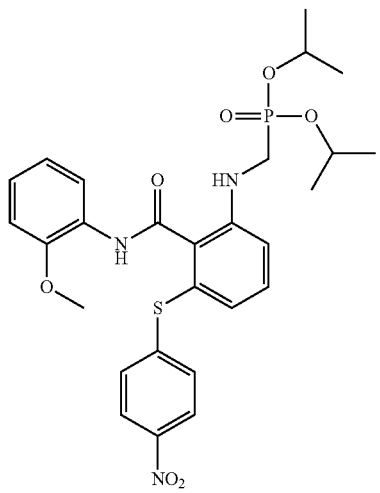 [SMILES: COc1ccccc1NC(=O)c1c(NCP(=O)(OC(C)C)OC(C)C)cccc1Sc1ccc([N+](=O)[O-])cc1]

Compound 25 (1.0 equiv.) was dissolved in MeCN (40 mL) and treated with anhydrous potassium carbonate (2.0 equiv.) at room temperature. To this mixture diisopropyl(bromomethyl)phosphonate (1.2 equiv.) was added via a micro syringe. After being stirred for 4 Hours at 60° C., the reaction mixture was concentrated under reduced pressure. The crude residue was diluted by ethyl acetate (50 mL), and washed with water (2×10 mL). Then it was dried over anhydrous Na₂SO₄, filtered, and concentrated under reduced pressure. The residue was purified by silica gel column chromatography (1:4 v/v ethyl acetate/petroleum ether) to provide a yellow solid (235.2 mg, 41% yield).

¹H NMR (400 MHz, DMSO) δ=1.28 (m, 12H), 3.33 (s, 3H), 3.83 (m, 2H), 5.31 (brs, 1H), 6.39 (d, J=8.0 Hz, 1H), 6.71 (t, J=7.6 Hz, 2H), 7.04 (t, J=7.6 Hz, 1H), 7.42 (m, 3H), 7.55 (d, J=8.0 Hz, 1H), 7.88 (d, J=8.0 Hz, 2H), 8.03 (d, J=8.0 Hz, 1H), 8.56 (s, 1H);

ESI-MS: [M+H]⁺ m/z 574.18

Example 30

General Procedure for 2-(2-aminoacetamido)-N-(2-methoxyphenyl)-6-(4-nitrophenylthio)benzamide hydrochloride (Compound 66)

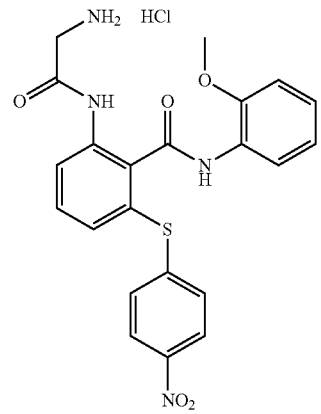 [SMILES: COc1ccccc1NC(=O)c1c(NC(=O)CN)cccc1Sc1ccc([N+](=O)[O-])cc1 ; Cl]

The compound 25 (1.0 equiv.), HOBt (1.2 equiv.) and EDCI (1.2 equiv.) were dissolved in DCM, stirring at room temperature. After that, glycine (1.0 equiv.) was slowly added into the mixture, stirring for 5 h. Then the reaction solution was concentrated under reduced pressure, and the concentrate was dissolved in ethyl acetate. The organic layer was once washed with brine, and dried over anhydrous Na₂SO₄. Then the organic layer was concentrated under reduced pressure. The concentrate with an appropriate amount of HCl was stirred for 2 hours, and filtered. The filter cake was washed with ethanol once and then washed with DCM to give a white solid; yield 45%;

¹H NMR (400 MHz, DMSO): 3.244 (s, 2 H), 3.684 (s, 3 H), 4.941 (br, 2 H), 6.915 (t, J=7.6 Hz, 1 H), 7.015 (d, J=8 Hz, 1 H), 7.131 (t, J=7.2 Hz, 1 H), 7.343 (m, 3 H), 7.548 (t, J=8 Hz, 1 H), 7.875 (d, J=8 Hz, 1 H), 8.111 (d, J=8.8 Hz, 2 H), 8.412 (d, J=8 Hz, 1 H), 9.904 (s, 1 H) ppm.

ESI-MS: [M+H]⁻ m/z 453.1.

Example 31

General Procedure for 2-(2-aminoacetamido)-N-(2-methoxyphenyl)-6-((4-nitrophenyl)sulfonyl)benzamide hydrochloride hydrochloride (Compound 67)

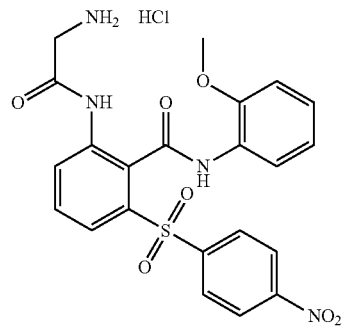 [SMILES: COc1ccccc1NC(=O)c1c(NC(=O)CN)cccc1S(=O)(=O)c1ccc([N+](=O)[O-])cc1 ; Cl]

Prepared by proceeding in similar manner to example 30, use compound 46 instead of compound 25. White solid; 51% yield;

$^1$H NMR (400 MHz, DMSO) δ=3.73 (S, 2H), 3.82 (S, 3H), 7.02 (t, J=6.8 Hz, 1H), 7.09 (d, J=7.6 Hz, 1H), 7.19 (t, J=7.2 Hz, 1H), 7.77 (t, J=6.8 Hz, 1H), 8.01 (t, J=7.6 Hz, 2H), 8.08 (d, J=7.6 Hz, 1H), 8.23 (d, J=8.4 Hz, 2H), 8.39 (m, 4H), 9.89 (S, 1H), 10.00 (br, 2H) ppm.

ESI-MS: [M+H]$^+$ m/z 485.

Example 32

General Procedure for 2-(2,6-diaminohexanamido)-N-(2-methoxyphenyl)-6-((4-nitrophenyl)thio)benzamide hydrochloride (Compound 68)

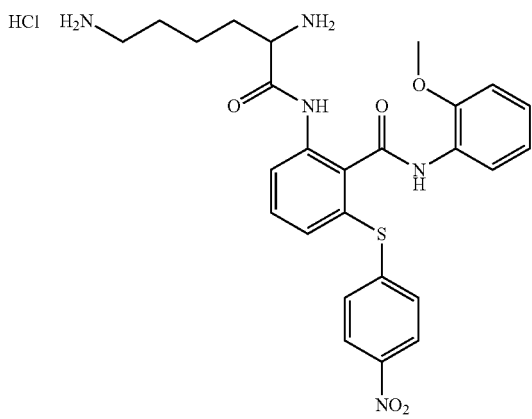 [SMILES: Cl ; COc1ccccc1NC(=O)c1c(NC(=O)C(N)CCCCN)cccc1Sc1ccc([N+](=O)[O-])cc1]

Prepared by proceeding in similar manner to example 30, use lysine of glycine. white solid; 39% yield;

$^1$H NMR (400 MHz, DMSO) δ=1.39 (m, 8H), 1.68 (S, 1H), 3.68 (S, 3H), 6.49 (S, 1H), 6.92 (t, J=7.6 Hz, 1H), 7.01 (d, J=8.0 Hz, 1H), 7.12 (t, J=7.6 Hz, 1H), 7.34 (m, 3H), 7.54 (t, J=7.6 Hz, 1H), 7.88 (d, J=7.6 Hz, 1H), 8.11 (d, J=8.0 Hz, 2H), 8.34 (d, J=8.0 Hz, 1H), 9.89 (S, 1H) ppm.

ESI-MS: [M+H]$^+$ m/z 524.

Example 33

General Procedure for 2-amino-N-(2-iodophenyl)-6-((4-nitrophenyl)thio)benzamide (Compound 71)

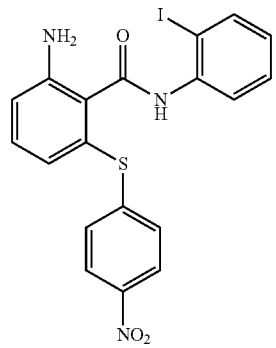 [SMILES: Nc1cccc(Sc2ccc([N+](=O)[O-])cc2)c1C(=O)Nc1ccccc1I]

Prepared by proceeding in similar manner to example 1, Yellow solid; 79% yield;

$^1$H NMR (400 MHz, CDCl$_3$) δ=4.61 (br, 2H), 6.86 (t, J=7.6 Hz, 2H), 6.99 (d, J=7.6 Hz, 1H), 7.28 (m, 4H), 7.78 (d, J=7.6 Hz, 1H), 8.03 (d, J=7.2 Hz, 3H), 8.11 (d, J=8.0 Hz, 1H) ppm.

ESI-MS: [M+Na]$^+$ m/z 514.

Example 34

General Procedure for 2-amino-N-(2-iodophenyl)-6-((4-nitrophenyl)sulfonyl)benzamide (Compound 72)

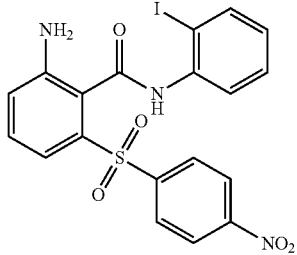 [SMILES: Nc1cccc(S(=O)(=O)c2ccc([N+](=O)[O-])cc2)c1C(=O)Nc1ccccc1I]

Prepared by proceeding in similar manner to example 7, White solid; 51.4% yield;

$^1$H NMR (400 MHz, CDCl$_3$) δ=4.36 (br, 2H), 6.99 (m, 2H), 7.40 (t, J=8.0 Hz, 1H), 7.46 (t, J=7.2 Hz, 1H), 7.53 (d, J=7.6 Hz, 1H), 7.78 (s, 1H), 7.86 (d, J=7.6 Hz, 1H), 8.13 (d, J=7.6 Hz, 2H), 8.20 (d, J=8.0 Hz, 1H), 8.30 (d, J=8.0 Hz, 2H) ppm.

ESI-MS: [M+Na]$^+$ m/z 546.

Example 35

General Procedure for 2-(2-amino-6-((4-nitrophenyl)thio)benzamildo)phenyl methanesulfonate (Compound 73)

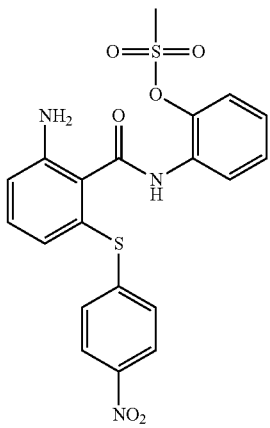 [SMILES: CS(=O)(=O)Oc1ccccc1NC(=O)c1c(N)cccc1Sc1ccc([N+](=O)[O-])cc1]

Prepared by proceeding in similar manner to example 1, Yellow solid; 56% yield;

$^1$H NMR (400 MHz, CDCl$_3$) δ=3.13 (S, 3H), 3.22 (S, 3H), 4.48 (br, 2H), 6.83 (d, J=8.0 Hz, 1H), 6.97 (d, J=2.8 Hz, 1H), 7.19 (t, J=7.2 Hz, 1H), 7.23 (m, 4H), 7.31 (t, J=8.0 Hz, 1H), 8.05 (m, 1H), 8.35 (S, 1H) ppm.

ESI-MS: [M+Na]$^+$ m/z 482.

Example 36

General Procedure for 2-amino-6-((3,5-dimethylphenyl)thio)-N-(2-methoxyphenyl)benzamide (Compound 74)

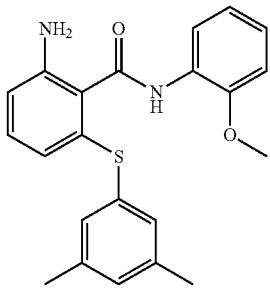 [SMILES: COc1ccccc1NC(=O)c1c(N)cccc1Sc1cc(C)cc(C)c1]

Prepared by proceeding in similar manner to example 1, White solid; 87.1% yield;

$^1$H NMR (400 MHz, CDCl$_3$) δ=2.20 (S, 6H), 3.78 (s, 3H), 4.54 (br, 2H), 6.63 (d, J=8.0 Hz, 1H), 7.69 (d, J=8.0 Hz, 1H), 6.87 (m, 2H), 6.89 (S, 2H), 6.97 (t, J=8.0 Hz, 1H), 7.08 (m, 2H), 8.42 (d, J=8.0 Hz, 1H), 8.48 (s, 1H) ppm.

ESI-MS: [M+Na]$^+$ m/z 401.

Example 37

General Procedure for 2-amino-6-((3,5-dimethylphenyl)sulfonyl)-N-(2-methoxyphenyl)benzamide (Compound 75)

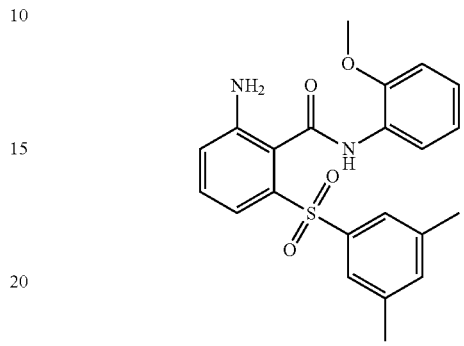

Prepared by proceeding in similar manner to example 7, Yellow solid; 62.8% yield;

$^1$H NMR (400 MHz, CDCl$_3$) δ=2.19 (S, 6H), 3.84 (S, 3H), 4.31 (br, 2H), 6.92 (t, J=8.0 Hz, 2H), 7.00 (t, J=8.0 Hz, 1H), 7.13 (m, 2H), 7.36 (m, 3H), 7.60 (d, J=8.0 Hz, 1H), 8.31 (d, J=8.0 Hz, 1H), 8.37 (S, 1H) ppm.

ESI-MS: [M+Na]$^+$ m/z 438.

Example 38

General Procedure for 4-((3-amino-2-((2-methoxyphenyl)carbamoyl)phenyl)thio)benzoic acid (Compound 76)

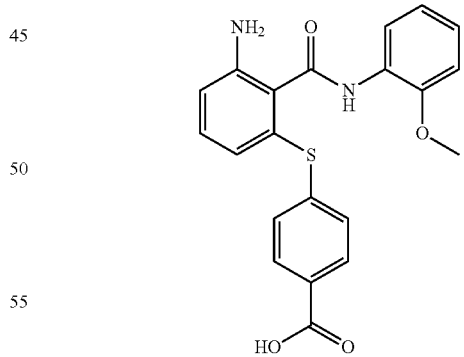

Prepared by proceeding in similar manner to example 1, Yellow solid; 36% yield;

$^1$H NMR (400 MHz, DMSO) δ=3.82 (S, 3H), 5.36 (br, 2H), 6.91 (t, J=8.0 Hz, 1H), 7.01 (d, J=8.0 Hz, 1H), 7.15 (m, 2H), 7.24 (d, J=8.0 Hz, 2H), 7.43 (d, J=8.0 Hz, 1H), 7.60 (d, J=8.0 Hz, 1H), 7.80 (d, J=8.0 Hz, 2H), 8.21 (S, 2H) ppm.

ESI-MS: [M+Na]$^+$ m/z 417.

Example 39

General Procedure for 4-((3-amino-2-((2-methoxyphenyl)carbamoyl)phenyl)sulfonyl)benzoic acid (Compound 77)

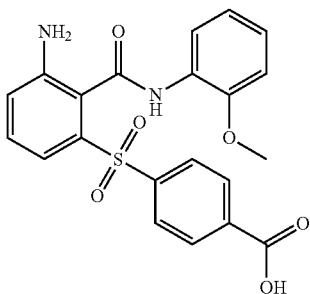 [SMILES: COc1ccccc1NC(=O)c1c(N)cccc1S(=O)(=O)c1ccc(C(=O)O)cc1]

Prepared by proceeding in similar manner to example 7, Yellow solid; 22% yield;

$^1$H NMR (400 MHz, DMSO) δ=3.78 (S, 3H), 5.55 (br, 2H), 7.03 (m, 2H), 7.09 (d, J=8.0 Hz, 1H), 7.23 (m, 2H), 7.34 (t, J=7.6 Hz, 1H), 7.77 (d, J=7.6 Hz, 1H), 8.04 (m, 4H), 9.60 (S, 1H), 13.480 (br, 1H) ppm.

ESI-MS: [M+Na]$^+$ m/z 449.

Example 40

General Procedure for 2-((2-aminoethyl)amino)-N-(2-methoxyphenyl)-6-((4-nitrophenyl)thio)benzamide (Compound 78)

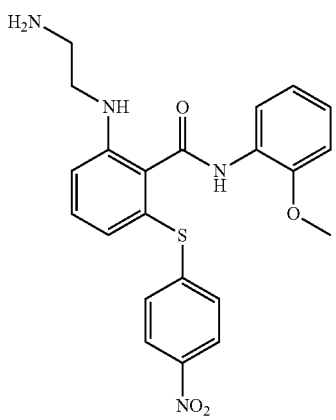 [SMILES: COc1ccccc1NC(=O)c1c(NCCN)cccc1Sc1ccc([N+](=O)[O-])cc1]

Prepared by proceeding in similar manner to example 9, Yellow solid; 51% yield;

$^1$H NMR (400 MHz, DMSO) δ=0.82 (m, 2H), 1.18 (m, 2H), 2.00 (br, 2H), 3.78 (S, 3H), 6.35 (m, 3H), 6.67 (t, J=7.6 Hz, 2H), 6.76 (m, 2H), 7.99 (d, J=8.0 Hz, 1H), 7.16 (m, 3H), 7.44 (d, J=8.0 Hz, 1H), 7.54 (S, 1H) ppm.

ESI-MS: [M+H]$^+$ m/z 439.

Example 41

General Procedure for 2-((2-aminoethyl)amino)-N-(2-methoxyphenyl)-6-((4-nitrophenyl)sulfonyl)benzamide (Compound 79)

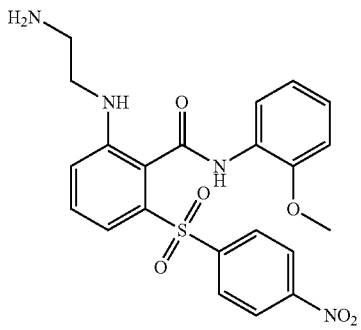 [SMILES: COc1ccccc1NC(=O)c1c(NCCN)cccc1S(=O)(=O)c1ccc([N+](=O)[O-])cc1]

Prepared by proceeding in similar manner to example 7, Yellow solid; 49% yield;

$^1$H NMR (400 MHz, DMSO) δ=0.85 (m, 2H), 1.26 (m, 2H), 2.09 (brs, 2H), 3.72 (s, 3H), 6.88 (d, J=8.0 Hz, 1H), 7.00 (m, 3H), 7.06 (s, 1H), 7.14 (t, J=7.6 Hz, 1H), 7.61 (t, J=8.0 Hz, 1H), 7.77 (d, J=8.0 Hz, 1H), 7.83 (d, J=8.0 Hz, 1H), 8.14 (d, J=9.2 Hz, 2H), 8.24 (d, J=7.2 Hz, 1H), 8.48 (s, 1H).

ESI-MS: [M+H]$^+$ m/z 471.

Example 42

General Procedure for 2-((2-hydroxyethyl)amino)-N-(2-methoxyphenyl)-6-((4-nitrophenyl)thio)benzamide (Compound 80)

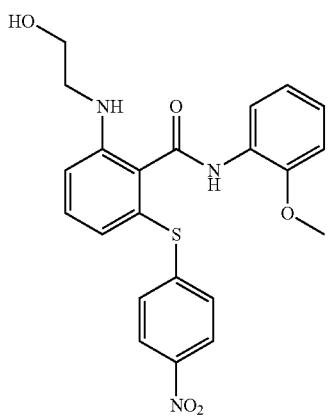 [SMILES: COc1ccccc1NC(=O)c1c(NCCO)cccc1Sc1ccc([N+](=O)[O-])cc1]

Prepared by proceeding in similar manner to example 9, Yellow solid; 66% yield.

$^1$H NMR (400 MHz, CDCl$_3$) δ=3.05 (t, J=8.0 Hz, 2H), 3.66 (m, 2H), 3.90 (s, 3H), 6.44 (d, J=8.0 Hz, 1H), 6.78 (d, J=8.0 Hz, 1H), 7.02 (m, 3H), 7.37 (m, 4H), 7.57 (m, 1H), 7.97 (d, J=7.2 Hz, 2H), 8.19 (s, 1H).

ESI-MS: [M+Na]$^+$ m/z 460

Example 43

General Procedure for 2-((2-hydroxyethyl)amino)-N-(2-methoxyphenyl)-6-((4-nitrophenyl)sulfonyl)benzamide (Compound 81)

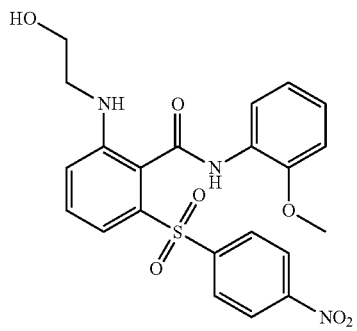 [SMILES: COc1ccccc1NC(=O)c1c(NCCO)cccc1S(=O)(=O)c1ccc([N+](=O)[O-])cc1]

Prepared by proceeding in similar manner to example 7, yellow solid; 43% yield;

$^1$H NMR (400 MHz, CDCl$_3$) δ=3.68 (m, 2H), 3.96 (t, J=8.4 Hz, 2H), 4.02 (s, 3H), 6.69 (d, J=8.0 Hz, 1H), 7.07 (t, J=8.0 Hz, 1H), 7.14 (d, J=8.0 Hz, 1H), 7.24 (m, 3H), 7.43 (m, 2H), 7.57 (d, J=8.0 Hz, 3H), 7.99 (d, J=7.6 Hz, 2H);

ESI-MS: [M+Na]$^+$ m/z 494.

Example 44

General Procedure for 2-((2-amino-2-oxoethyl)amino)-N-(2-methoxyphenyl)-6-((4-nitrophenyl)thio)benzamide (Compound 82)

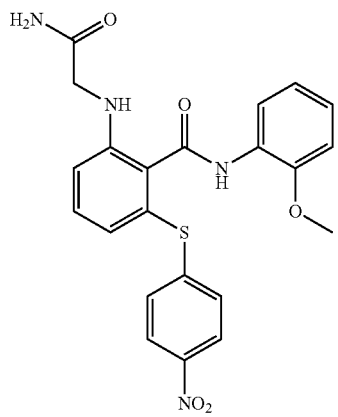 [SMILES: COc1ccccc1NC(=O)c1c(NCC(N)=O)cccc1Sc1ccc([N+](=O)[O-])cc1]

Prepared by proceeding in similar manner to example 9, White solid; 86.1% yield;

$^1$H NMR (400 MHz, DMSO) δ=3.78 (s, 3H), 5.34 (brs, 2H), 5.85 (s, 2H), 6.46 (m, 2H), 6.67 (t, J=7.2 Hz, 2H), 6.76 (t, J=7.2 Hz, 2H), 6.99 (d, J=8.0 Hz, 2H), 7.16 (m, 3H), 7.43 (d, J=7.2 Hz, 1H), 7.55 (s, 1H).

ESI-MS: [M+H]$^+$ m/z 453.

Example 45

General Procedure for 2-(2-amino-3-phenylpropanamido)-N-(2-methoxyphenyl)-6-((4-nitrophenyl)sulfonyl)benzamide (Compound 83)

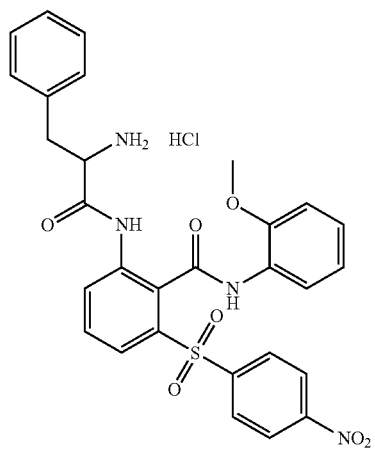 [SMILES: COc1ccccc1NC(=O)c1c(NC(=O)C(N)Cc2ccccc2)cccc1S(=O)(=O)c1ccc([N+](=O)[O-])cc1 ; Cl]

Prepared by proceeding in similar manner to example 31, Yellow solid; 43% yield;

$^1$H NMR (400 MHz, DMSO) δ=2.88 (m, 1H), 3.14 (d, J=16.0 Hz, 2H), 3.44 (d, J=8.0 Hz, 1H), 3.69 (s, 3H), 4.35 (brs, 2H), 6.99 (m, 2H), 7.12 (t, J=8.0 Hz, 1H), 7.23 (d, J=8.0 Hz, 4H), 7.77 (t, J=8.0 Hz, 1H), 7.94 (d, J=4.0 Hz, 1H), 8.10 (d, J=8.0 Hz, 1H), 8.31 (m, 7H), 9.88 (s, 1H).

ESI-MS: [M+H]$^+$ m/z 575.

Biological Activity Tests

The anti-HIV activity was determined by the "Guiding Principles of Anti HIV Drug Unclinical Pharmacodynamics" of SFDA which is tested by technology standard assay according to International Universal Standards and Methods. The results are shown in Table 1. Where in $CC_{50}$, $EC_{50}$ were measured twice and took the average.

From Table 1, we can see that most of the compounds can inhibit HIV in vitro. Especially compound 25, 46, 67 and 83, which bearing high efficiency, low toxicity and high TI. Thus these compounds are suitable to be novel inhibitors of vif for anti-HIV.

FIG. 1

| | C8166 cells | | | H9 cells | | |
|---|---|---|---|---|---|---|
| compound | $CC_{50}$ | $EC_{50}$ | TI | $CC_{50}$ | $EC_{50}$ | TI |
| 22 | 107.83 | >200 | 0.54 | >200 | >200 | — |
| 23 | >200 | >200 | — | >200 | >200 | — |
| 24 | 172.21 | 2.59 | 66.58 | >200 | 2.62 | >76.34 |
| 25 | 65.40 | 0.21 | 310.02 | 152.94 | 0.74 | 206.68 |
| 27 | 80.57 | 24.03 | 3.35 | 123.48 | 98.45 | 1.25 |
| 28 | 93.04 | 83.84 | 1.11 | 77.23 | 98.45 | 0.78 |
| 29 | 109.72 | 73.50 | 1.49 | 74.62 | >200 | <0.37 |
| 45 | >200 | 0.367 | 385.34 | 117.08 | 1.66 | 70.53 |
| 46 | 140.59 | 0.096 | 2081.59 | >200 | 0.66 | >303.03 |
| 47 | — | — | — | 137.82 | 4.3 | 32.05 |
| 48 | — | — | — | 76.60 | 35.87 | 2.14 |
| 49 | — | — | — | >200 | 41.50 | 4.82 |
| 50 | — | — | — | 81.06 | 28.29 | 2.87 |
| 51 | — | — | — | 18.09 | 18.84 | 0.96 |
| 52 | — | — | — | >200 | >200 | — |
| 53 | — | — | — | >200 | 43.69 | >4.58 |
| 54 | — | — | — | 85.79 | 83.93 | 1.02 |
| 55 | >200 | >200 | — | >200 | >200 | — |
| 56 | >200 | 24.48 | >8.17 | >200 | 137.08 | >1.46 |
| 57 | 37.24 | 14.07 | 2.65 | >200 | 16.81 | >11.90 |

-continued

FIG. 1

| | C8166 cells | | | H9 cells | | |
|---|---|---|---|---|---|---|
| compound | $CC_{50}$ | $EC_{50}$ | TI | $CC_{50}$ | $EC_{50}$ | TI |
| 58 | >200 | 99.97 | >2.00 | >200 | 102.89 | >1.94 |
| 59 | >200 | 63.68 | >3.14 | 88.39 | 122.90 | 0.72 |
| 60 | >200 | 91.32 | >2.19 | >200 | >200 | — |
| 61 | >200 | 46.94 | >4.26 | >200 | >200 | — |
| 62 | 10.25 | 3.43 | 2.99 | 14.22 | 3.83 | 3.71 |
| 63 | >200 | 53.31 | >3.75 | >200 | >200 | — |
| 64 | 10.424 | 3.17 | 3.28 | 17.83 | 21.01 | 0.85 |
| 65 | 18.789 | 105.78 | 0.18 | 25.41 | >200 | 0.13 |
| 66 | 78.263 | 0.81 | 97.01 | 72.27 | 0.16 | 451.69 |
| 67 | 165.488 | 0.43 | 388.04 | 94.87 | 0.12 | 790.58 |
| 68 | 115.617 | 0.94 | 122.45 | 90.09 | 2.38 | 37.85 |
| 71 | >200 | 61.44 | >3.26 | >200 | >200 | — |
| 72 | >200 | 16.19 | >12.35 | >200 | 192.60 | 1.04 |
| 73 | 194.07 | 36.73 | 5.28 | >200 | >200 | — |
| 74 | 68.60 | 7.26 | 9.45 | >200 | >200 | — |
| 75 | >200 | >200 | — | >200 | >200 | — |
| 76 | >200 | 92.05 | >2.17 | >200 | 100.3 | 1.99 |
| 77 | >200 | >200 | — | >200 | >200 | — |
| 78 | 24.23 | 16.94 | 1.43 | 16.75 | 19.91 | 0.84 |
| 79 | 90.86 | 93.53 | 0.97 | 99.47 | 100.82 | 0.99 |
| 80 | 93.51 | 19.44 | 4.81 | 116.38 | 19.15 | 6.08 |
| 81 | 102.26 | 89.10 | 1.15 | 72.70 | 101.99 | 0.71 |
| 82 | >200 | >200 | — | >200 | >200 | — |
| 83 | 178.23 | 0.45 | 396.07 | 102.44 | 0.15 | 682.93 |

$CC_{50}$, $EC_{50}$ (μg/mL)

Compound 67 and 83 are prodrugs of compound 46 (In C8166 TI=2081.59, in H9 TI=303.03). It was proved that they were hydrolyzed into 46 in vivo. It should be noted that the prodrugs also have the anti-HIV activity of their own (In C8166 TI=388.04 and 291.4, in H9 TI=790.58 and 756.32).

| FIG. 1: Anti-HIV-1 activities of 67 and 46 | | | | | | |
|---|---|---|---|---|---|---|
| | C8166 | | | H9 | | |
| compound | $CC_{50}$ (μg/mL) | $EC_{50}$ (μg/mL) | TI | $CC_{50}$ (μg/mL) | $EC_{50}$ (μg/mL) | TI |
| 67 | 165.488 | 0.43 | 388.04 | 94.87 | 0.12 | 790.58 |
| 46 | 140.59 | 0.096 | 2018.59 | >200 | 0.66 | >303.03 |

The anti-HIV activities of 46 against different resistant viruses were also tested and showing low toxicity toward mutant strain. 46 can inhibit the pathological changes of C8166 induced by HIV-1$_{IIIB}$ as well as the reproduction of viruses in H9 cells. 46 has a good inhibition on HIV-1$_{74V}$, HIV-1$_{A17}$, and HIV-1$_{L10R/M46I/L63P/V82T/I84V}$ as well as Clinical isolated strain such as HIV-1$_{KM018}$ and HIV-1$_{TC-1}$. (Table 2).

Figure 2:
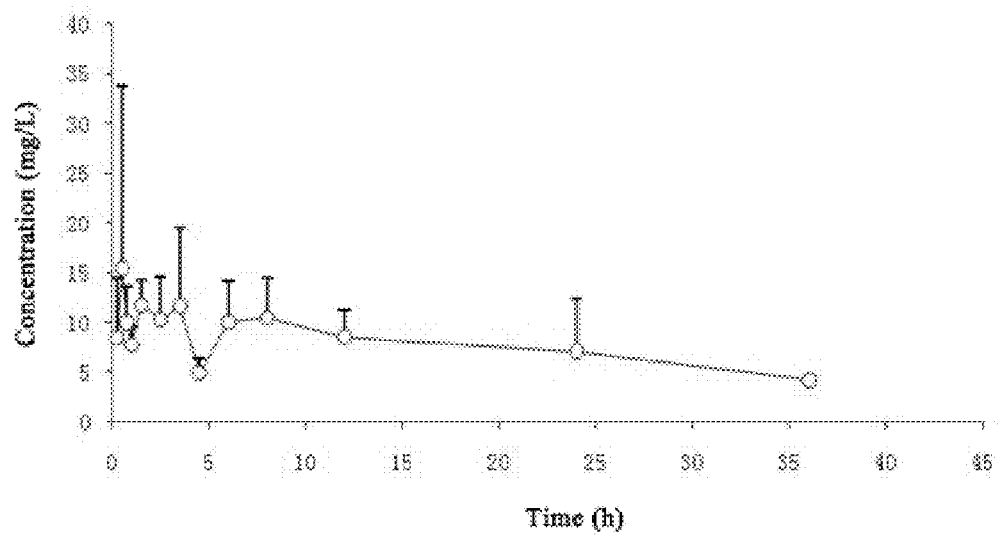
FIG. 2 shows a plasma concentration image of compound 67 at 50 mg/Kg by intravenous.
Figure 3:
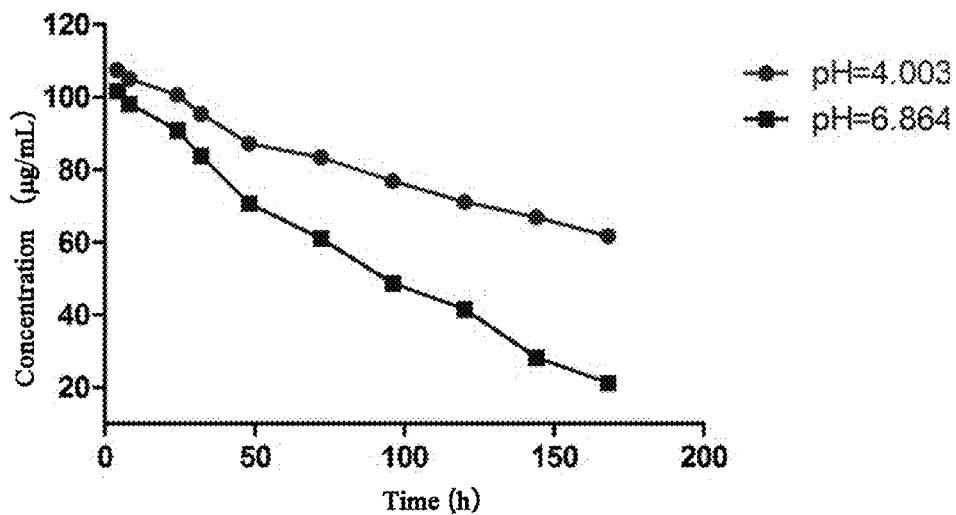
FIG. 3 shows a degradation image of compound 67 in weak acid solution.

| FIG. 2: Anti-HIV-1 activities of 46 in cell cultures[a] | | |
|---|---|---|
| Virus | $EC_{50}$ (μg/mL) | TI ($CC_{50}/EC_{50}$) |
| HIV-1$_{IIIB}$ (C8166 cells) | 0.096 | 2081.59 |
| HIV-1$_{IIIB}$ (H9 cells) | 0.66 | >303.03 |
| HIV-1$_{74V}$ | 0.81 | 173.57 |
| HIV-1$_{A17}$ | 18.72 | >20 |
| HIV-1$_{L10R/M46I/L63P/V82T/I84V}$ | 0.83 | 169.39 |
| HIV$_{KM018}$ | 6.23 | >31.65 |
| HIV-1$_{TC-1}$ | 0.11 | >1818.18 |

[a]C8166 cells and H9 cells: human T-lymphoma cell line; HIV-1$_{IIIB}$ and HIV-1$_{74V}$: NNRTI-resistant virus strains; HIV-1$_{A17}$: NVP resistant virus strains; HIV-1$_{L10R/M46I/L63P/V82T/I84V}$: PI-resistant virus strains; HIV$_{KM018}$ and HIV-1$_{TC-1}$: clinical strains.

Meanwhile these compounds have good therapeutic effect in HIV-2. Compound 25, 46, 67 and 83 bear high TI and low toxicity.

TABLE 3 the active of compound 25, 46, 67
for HIV-2 ROD and HIV-2CBL-20

| | HIV-2 ROD | | | HIV-2 CBL-20 | | |
|---|---|---|---|---|---|---|
| compound | $CC_{50}$ (μg/ml) | $EC_{50}$ (μg/ml) | TI | $CC_{50}$ (μg/ml) | $EC_{50}$ (μg/ml) | TI |
| 25 | 184.61 | 0.59 | 312.90 | 163.77 | 0.82 | 199.72 |
| 46 | >200 | 0.41 | 487.8 | >200 | 0.45 | 444.44 |
| 67 | 126.19 | 0.78 | 161.78 | 106.26 | 1.21 | 87.82 |

HIV-2 ROD Separated and got at Senegal in 1985; HIV-2CBL-20 Separated and got at Gambia.

Solubility is an important parameter of druggability. The solubility of prodrugs 66, 67 and 68 are good. The solubility of 67 in water with pH=7 can be as good as 1730.64 μg/ml. The solubility of 66 and 68 in aqueous solution (pH=2) can reach 1290 and 2845.5 μg/ml. They are with good solubility and can be formulated into an oral formulation. The prodrugs can be hydrolyzed into 46 which is with good fat-solubility and TI as well as distribution.

In pharmacokinetics, after oral gavage of 67 by 100 mg/kg, the max blood concentration of 46 can be as high as 21.662 μg/ml and it can be released in many times in vivo, reaching a bioavailability of 161.2%. (FIG. 1 and FIG. 2)

The Metabolism of 67 to 46 Medicine Curve and Bioavailability

| | Cmax (mg/L) | AUC(0~)9 (mg/L * h) | CL (L/h/kg) | F (%) |
|---|---|---|---|---|
| oral (100 mg/kg) | 21.662 | 387.758 | 4.878 | 162.2 |
| Intravenous (50 mg/kg) | 326.494 | 120.282 | 0.453 | |

In toxicity test, the acute toxicity test of 67 and 46 were tested and no abnormal phenomenon occurred.

In pharmacodynamics, results show that 46 and its prodrug 67 are very safe even at a high dose (10 g/kg).

Figure 4:
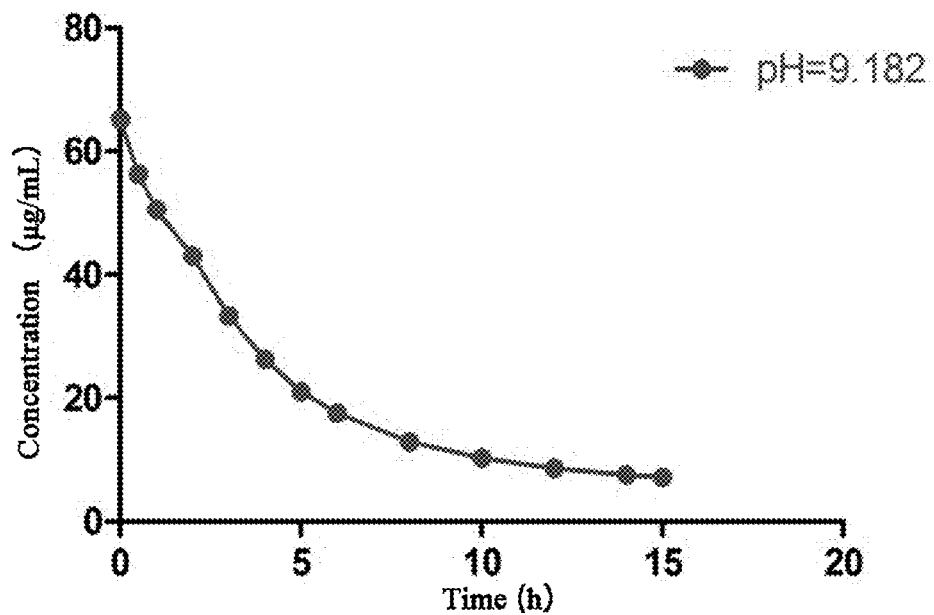
FIG. 4 shows a degradation image of compound 67 under mild alkaline conditions.
Figure 5:
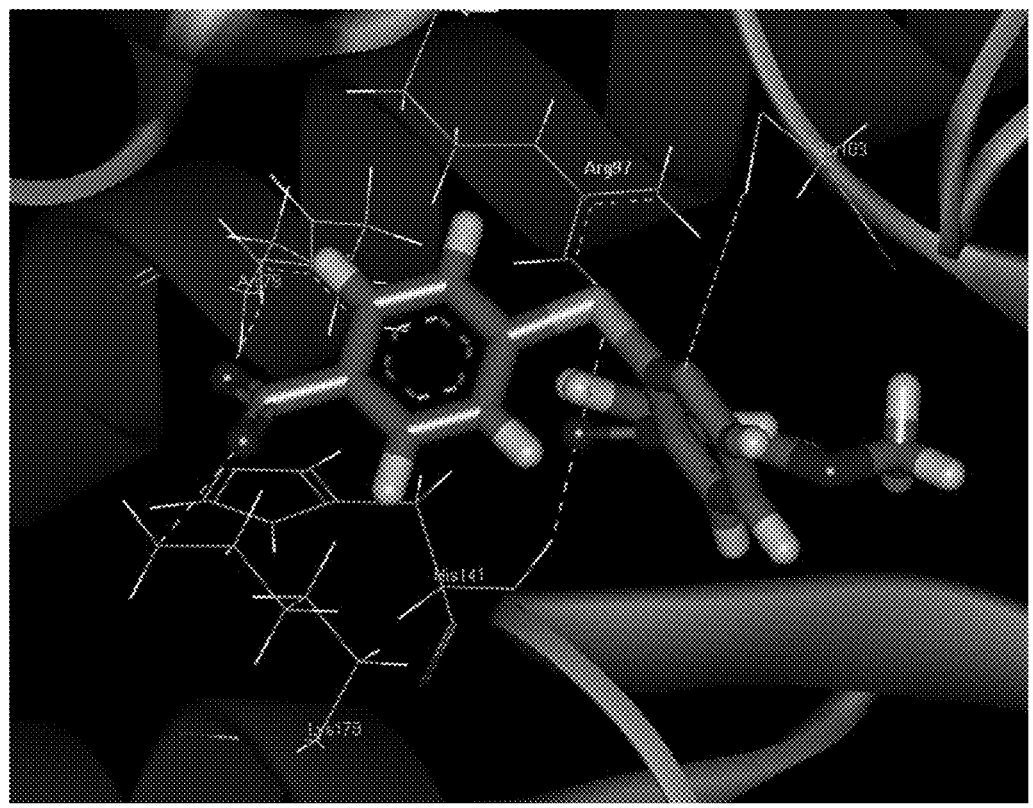
FIG. 5 shows a possible binding mode between Vif and compound 46.

As for the stability of the drugs, those prodrugs possess the favorable stability by experimentation. For example, compound 67 was tested in solutions with PH=4.004, 6.864 and 9.182, and its degradation rate was 0.2767, 0.4956 and 9.182, respectively. 67 possess the favorable stability in acid condition while they prone to be hydrolyzed in alkaline solution. As to the Mechanism of action of the compounds, the possible binding mode between 46 and vif was predicted by docking There are five possible hydrogen bonds between them: two hydrogen bonds between the nitro group and Arg79 and Lys178, two hydrogen bonds between the oxygen atom of methoxyl group with His141 and Arg97, one hydrogen bond between the nitrogen atom of pyridine with Gly103. (The binding mode can be seen in FIG. 4)

The invention claimed is:

1. An anti-HIV compound represented by the following formula

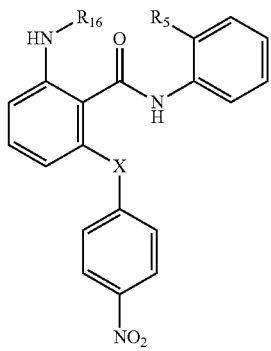

wherein:
R$_5$ is a straight chain or branched C$_{1-8}$ alkoxy group;
X is S or SO$_2$; and
R$_{16}$ is H or

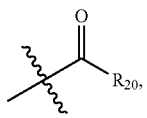

where R$_{20}$ is at least one amino acid selected from the group consisting of Ala, Arg, Asn, Asp, Cys, Glu, Gln, Gly, His, Ile, Leu, Lys, Met, Phe, Pro, Ser, Thr, Trp, Tyr and Val, provided that the at least one amino acid that is directly connected to the carbonyl group of R$_{16}$ is free of an α-C carboxyl group.

2. The compound according to claim 1, wherein R$_{16}$ is H.

3. The compound according to claim 2, wherein R$_5$ is a C$_{1-4}$ alkoxy group.

4. The compound according to claim 3, wherein R$_5$ is a C$_{1-2}$ alkoxy group.

5. The compound according to claim 3, wherein R$_5$ is methoxyl.

6. The compound according to claim 1 having a structure selected from the group consisting of:

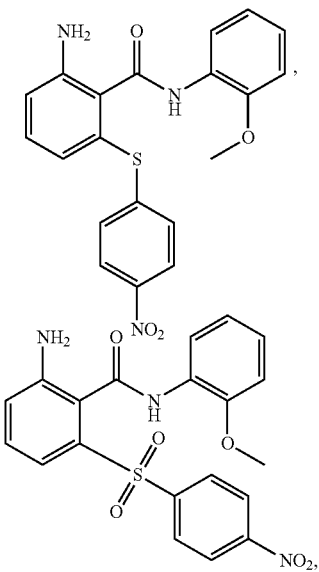

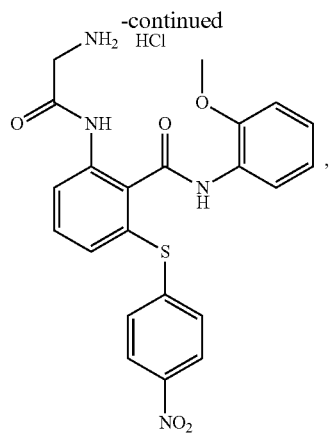

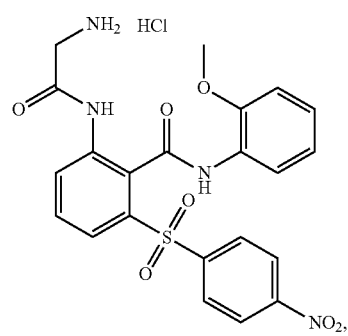

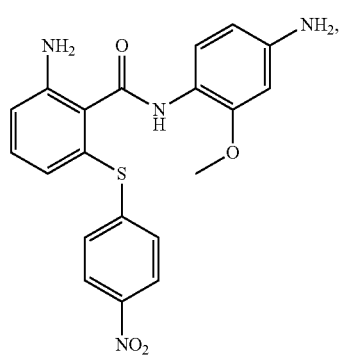

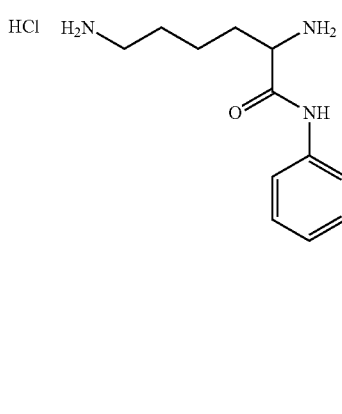

and

-continued

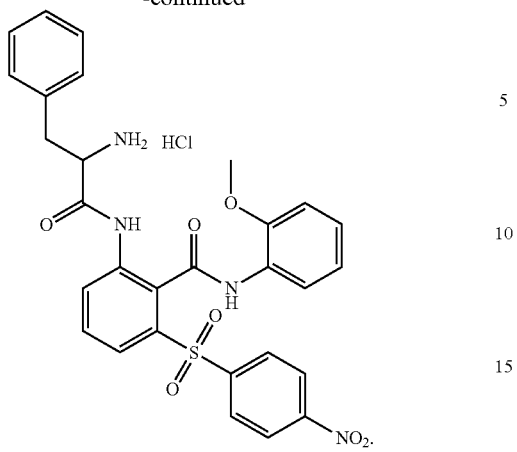

5

7. A pharmaceutically acceptable salt of a compound according to claim 1, wherein the salt is a hydrochloride, sulfate, phosphate or nitrate salt.

8. The pharmaceutically acceptable salt according to claim 7, which is the hydrochloride salt.

9. A method for treating HIV, said method comprising administering to a patient a compound according to claim 1.

10. The method of claim 9, wherein the compound is effective for treating at least one of HIV-1 and HIV-2 infection.

* * * * *